US009687523B2

(12) United States Patent
Hamm-Alvarez

(10) Patent No.: US 9,687,523 B2
(45) Date of Patent: Jun. 27, 2017

(54) COMPOSITIONS AND METHODS FOR THE TREATMENT OF SJÖRGREN'S SYNDROME

(75) Inventor: Sarah Hamm-Alvarez, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 53 days.

(21) Appl. No.: 12/931,601

(22) Filed: Feb. 3, 2011

(65) Prior Publication Data

US 2011/0257103 A1 Oct. 20, 2011

Related U.S. Application Data

(60) Provisional application No. 61/301,535, filed on Feb. 4, 2010.

(51) Int. Cl.

| | |
|---|---|
| ***A61P 27/02*** | (2006.01) |
| ***A61P 37/06*** | (2006.01) |
| ***A61K 38/17*** | (2006.01) |
| ***A61K 31/436*** | (2006.01) |

(52) U.S. Cl.

CPC ............ *A61K 38/17* (2013.01); *A61K 31/436* (2013.01)

(58) Field of Classification Search

CPC C07K 14/4713; C12N 2501/04; A61K 38/17; A61K 31/436

See application file for complete search history.

(56) References Cited

U.S. PATENT DOCUMENTS

| | | | |
|---|---|---|---|
| 5,006,310 A | 4/1991 | Gin et al. | |
| 5,100,899 A * | 3/1992 | Calne | 514/291 |
| 6,160,095 A | 12/2000 | Chaudhary et al. | |
| 6,190,691 B1 * | 2/2001 | Mak | 424/449 |
| 2004/0229863 A1 | 11/2004 | Cummings et al. | |
| 2007/0086979 A1 * | 4/2007 | Chevrier et al. | 424/85.1 |
| 2009/0258828 A1 | 10/2009 | Beuerman et al. | |
| 2009/0263825 A1 | 10/2009 | Castro | |
| 2011/0224133 A1 | 9/2011 | Jung et al. | |
| 2012/0171221 A1 | 7/2012 | Hamm-Alvarez et al. | |
| 2012/0183568 A1 | 7/2012 | Hamm-Alvarez | |

FOREIGN PATENT DOCUMENTS

| | | |
|---|---|---|
| CN | 1858059 A | 11/2006 |
| WO | WO 2006/010041 A2 | 1/2006 |
| WO | WO-2006/062626 A1 | 6/2006 |
| WO | WO 2010/011952 | 1/2010 |
| WO | WO 2011/005779 | 1/2011 |
| WO | WO 2012/015836 | 2/2012 |

OTHER PUBLICATIONS

Alberts et al. 1994. Molecular Biology of the Cell, Third Edition, Garland Publishing, Inc. New York & London, pp. 129-130.*

Jabs et al. Inflammatory mediators in autoimmune lacrimal gland disease in MRL/Mpj mice. Invest Ophthalmol Vis Sci. Jul. 2004;45(7):2293-8.*

Fang et al. Effect of transgenic overexpression of FLIP on lymphocytes on development and resolution of experimental autoimmune thyroiditis. Am J Pathol. Sep. 2011;179(3):1211-20. doi: 10.1016/j.ajpath.2011.05.054. Epub Jul. 16, 2011.*

Ozturk et al. Cellular FLICE-like inhibitory proteins (c-FLIPs): fine-tuners of life and death decisions. Exp Cell Res. Jul. 1, 2012;318(11):1324-31. doi: 10.1016/j.yexcr.2012.01.019. Epub Jan. 28, 2012.*

Fiore et al. Pain in the quiet (not red) eye. Am Fam Physician. Jul. 1, 2010;82(1):69-73.*

Benito et a. Sirolimus (rapamycin) for the treatment of steroid-refractory acute graft-versus-host disease. Transplantation. Dec. 27, 2001;72(12):1924-9.*

Shah et al. A rapamycin-binding protein polymer nanoparticle shows potent therapeutic activity in suppressing autoimmune dacryoadenitis in a mouse model of Sjögren's syndrome. J Control Release. Nov. 10, 2013;171(3):269-79. Epub Jul. 25, 2013.*

U.S. Appl. No. 13/812,482, filed Jul. 26, 2011, Jung.

Azuma et al., "Identification of candidate genes for Sjogren's Syndrome using MRL/1pr mouse model of Sjogren's Syndrome and cDNA microarray analysis," Immunology Letters 81(3):171-176 (2002).

Caffery et al., "Tear lipocalin and lysozyme in Sjoegren and non-Sjoegren dry eye," Optometry and Vision Science 85(8):661-667 (2008).

Centola et al., "Genome-scale assessment of molecular pathology in systemic autoimmune diseases using microarray technology: a potential breakthrough diagnostic and individualized therapy-design tool," Scandinavian Journal of Immunology 64(3): 236-242 (2006).

Database WPI Week 200751, 2007-514150.

Flanagan et al., "Role of lactoferrin in the tear film," Biochimie 91(1): 35-43 (2009).

Kim et al., "Exogenous tumour necrosis factor alpha induces suppression of autoimmune arthritis," Arthritis Research and Therapy 10(1):R38 (2008).

Lee et al., "FLIP-mediated autophagy regulation in cell death control," Nature Cell Biology 11(11):1355-62 (2009).

Link et al., "Advances in cathepsin S inhibitor design," Current Opinion in Drug Discovery and Development 9(4): 471-482 (2006).

Schenke-Layland et al., "Lymphocytic infiltration leads to degradation of lacrimal gland extracellular matrix structures in NOD mice exhibiting a Sjogren's Syndrome-like exocrinopathy," Experimental Eye Research 90(2): 223-237 (2010).

(Continued)

*Primary Examiner* — Gregory S Emch

(74) *Attorney, Agent, or Firm* — Foley & Lardner LLP; Antoinette F. Konski; Peng Sun

(57) ABSTRACT

This invention provides a method of inducing a lacrimal acinar cell in a tissue to degrade a secretory vesicle and its content protein or proteins from the trans-Golgi network (TGN) by contacting the cells with an effective amount of an agent that induces autophagy. Also provided is a method for treating a mammal suffering from defective trans-Golgi network-secretory vesicle (TGN-SV) sorting by administering to the mammal an effective amount of an agent that induces autophagy in the tissue having the defective TGN-SV.

4 Claims, 7 Drawing Sheets

(56) References Cited

OTHER PUBLICATIONS

Shintani et al., "Autophagy in health and disease: a double-edged sword," Science 306(5698):990-995,986 (2004).
Sir et al., "Aotophagy in viral replication and pathogenesis," Molecules and Cells, pp. 1-7 http://www.springerlink.com/content/w11863514686481 5/fulltext.pdf (2010).
Sohar et al., "Lysosomal enzyme activities: new potential markers for Sjogren's Syndrome," Clinical Biochemistry 38(12): 1120-1126 (2005).
Taubert et al., "Expression of cathepsin B, D and L protein in juvenile idiopathic arthritis," Autoimmunity 35(3): 221-224 (2002).
Wu et al., "Altered expression of genes functioning in lipid homeostasis is associated with lipid deposition in NOD mouse lacrimal gland," Experimental Eye Research 89(3): 319-332 (2009).
Ye et al., "Kaposi's sarcoma-associated herpesvirus latent gene vFLIP inhibits viral lytic replication through NF-kappa B-mediated suppression of the AP-1 pathway: a novel mechanism of virus control of latency," Journal of Virology 82(9): 4235-4249 (2008).
American Dental Association, "Potential Salivary Biomarkers Identified for Detecting Primary Sjogren's Syndrome," taken from www.ada.org/3142.aspx, printed on Mar. 23, 2012.
Araki et al. "Th1/Th2 cytokine levels in the tear fluid of patients with Sjogren's Syndrome", Investigative Ophthalmology and Visual Science, 46: E-abstract 4464 (2005).
Barabino et al., "Animal Models of Dry Eye: A Critical Assessment of Opportunities and Limitations," Invest Ophthalmol Vis Sci. 45(6):1641-1646 (2004).
Flo et al., "Lipocalin 2 Mediates an Innate Immune Response to Bacterial Infection by Sequestrating Iron," Nature 432:917-921 (2004).
Franceschini et al., "Anti-Ro/SSA and La/SSB antibodies," Autoimmunity 38 (1):55-63 (2005).
Ghibaudi et al., "Unraveling the Catalytic Mechanism of Lactoperoxidase and Myeloperoxidase," Eur. J. Biochem. 270:4403-4412 (2003).
Gibson et al., "Diagnostic and prognostic biomarker discovery strategies for autoimmune disorders", Journal of Proteomics 73:1045-1060 (2010).
Gupta et al., "Cysteine Cathepsin S as an Immunomodulatory Target: Present and Future Trends," Expert Opin Ther Targets, 12(3):291-299 (2008).
Hu et al., "Preclinical Validation of Salivary Biomarkers for Primary Sjogren's Syndrome," Arthritis Care & Research, 62(11):1633-1638 (2010).
Hu et al., "Salivary Proteomic and Genomic Biomarkers for Primary Sjogren's Syndrome," Arthritis Rheum., 56(11):3588-3600 (2007).
International Search Report for PCT/US2010/041092, dated Jan. 20, 2011, 5 pages.
Katunuma et al., "Structure Based Development of Novel Specific Inhibitors for Cathepsin L and Cathepsin S in Vitro and in Vivo," FEBS Letters 458:6-10 (1999).
Li et al. "Increased expression of cathepsins and their regulatory cytokines in the lacrimal gland of male NOD mouse" Investigative Ophthalmology and Visual Science 49: E-abstract 425 (2008).
Li et al., "Increased Expression of Cathepsins and Their Regulatory Cytokines in the Lacrimal Gland of Male NOD Mouse," presented at ARVO Annual Meeting, Fort Lauderdale, Florida, Apr. 27-May 1, 2008.
Liu et al., "Increased Serum Cathepsin S in Patients with Atherosclerosis and Diabetes," Atherosclerosis, 186: 411-419 (2006).
Meijer et al., "The Future of Biologic Agents in the Treatment of Sjogren's Syndrome," Clin Rev Allergy Immunol 32:292-297 (2007).
Nazmul-Hossain, "Validation of Salivary-Biomarkers for Sjogren's Syndrome Detection in US population," International & American Associations for Dental Research, presented on Mar. 19, 2011.
Nguyen et al., "Differential Gene Expression in the Salivary Gland During Development and Onset of Xerostomia in Sjogren's Syndrome-like Disease of the C57BL/6.NOD-Aec1Aec2 Mouse," Arthritis Res. Ther., 11(2):R56 (2009).
Nguyen et al., "Differential Gene Expressions in the Lacrimal Gland During Development and Onset of Keratoconjunctivitis Sicca in Sjogren's Syndrome (SJS)-like Diseases of the C57BL/6.NOD-Aec1Aec2 Mouse," Exp Eye Res., 88(3):398-409 (2009).
Prince, "Biomarkers for diagnosing and monitoring autoimmune diseases," Biomarkers. 10(Supplement 1):S44-S49 (2005).
Saegusa et al., "Cathepsin S inhibitor prevents autoantigen presentation and autoimmunity", The Journal of Clinical Investigation, 11(3):361-369 (2002).
Small et al., "The Emerging Relevance of the Cysteine Protease Cathepsin S in Disease" Clinic Rev Bone Miner Metab., 9:122-132 (2011).
Tektonidou et al., "Validity of clinical associations of biomarkers in translational research studies: the case of systemic autoimmune disease," Arthritis Research and Therapy. 12(R179): 1-10 (2010).
Tomosugi et al., "Diagnostic Potential of Tear Proteomic Patterns in Sjogren's Syndrome," J. Proteome Res., 4(3):820-825 (2005).
Turk et al., "Lysosomal Cysteine Proteases: Facts and Opportunites," EMBO J. 20(17):4629-4633 (2001).
US Office Action for U.S. Appl. No. 13/324,963 dated Aug. 20, 2013.
US Office Action for U.S. Appl. No. 13/324,963 dated Aug. 20, 2014.
US Office Action for U.S. Appl. No. 13/382,286 dated Jan. 26, 2015.
US Office Action for U.S. Appl. No. 13/382,286 dated Feb. 27, 2014.
US Office Action for U.S. Appl. No. 13/382,286 dated Jun. 6, 2013.
US Restriction Requirement for U.S. Appl. No. 13/324,963 dated Nov. 20, 2012.
US Restriction Requirement for U.S. Appl. No. 13/382,286 dated Nov. 8, 2012.
Weinberg, "Antibiotic Properties and Applications of Lactoferrin" Curr Pharm Des. 13(8):801-811.
Wu et al., "Gene Expression of Apolipoproteins in Human Lacrimal Gland," Abstract, believed to be available by Dec. 2009 (6240-D851 on 2nd page).
Wu et al., "Genes Encoding Salivary Gland-Enriched Proteins Exhibit Increased Expression in Diseased Lacrimal Glands from Male NOD Mice," presented at the Association for Research in Vision and Ophthalmology, May 2008.
Zimecki et al., "Milk-derived Proteins and Peptides of Potential Therapeutic and Nutritive Value," . Exp Ther. Oncol. 6(2):89-106 (2007).
Zoukhri et al., "Role of Proinflammatory Cytokines in the Impaired Lacrimation Associated With Autoimmune Xerophthalmia," Invest Ophthalmol Vis Sci. 43(5):1429-1436 (2002).
Sada, P.R. et al. (2014) "Biologic treatment in SS," Rheumatology:1-12.
Keystone, E.C. (2004) "The utility of tumour necrosis factor blockade in orphan diseases," Ann. Rheum. Dis. 63(Suppl II):ii79-ii83.
Final Office Action in U.S. Appl. No. 13/324,963 dated Apr. 1, 2015.
Final Office Action in U.S. Appl. No. 13/382,286 dated Nov. 5, 2015.
Pajak B. et al. (2012), "Verapamil-induced autophagy-like process in colon adenocarcinoma COLO 205 cells; the ultrastructural studies", Pharmacol. Rep. 2012; 64:991-996.
Rubinsztein D. C. et al. (2012), "Autophagy modulation as a potential therapeutic target for diverse diseases", Nature Review, Drug Discovery 11(9):709-730, Sep. 2012.
Advisory Action for U.S. Appl. No. 13/324,963, dated Apr. 15, 2014, 3 pages.
Final Office Action for U.S. Appl. No. 13/324,963, dated Jan. 8, 2014, 14 pages.
Non-Final Office Action for U.S. Appl. No. 13/324,963, dated Jun. 1, 2016, 10 pages.
Restriction Requirement for U.S. Appl. No. 13/324,963, dated Jun. 10, 2013, 15 pages.
US Office Action dated Oct. 18, 2016, from U.S. Appl. No. 13/324,963.
US Notice of Allowance dated Nov. 9, 2016, U.S. Appl. No. 13/324,963.

(56) References Cited

OTHER PUBLICATIONS

US Office Action dated Mar. 24, 2017, from U.S. Appl. No. 13/382,286.

* cited by examiner

A.

B.

C.

D.

A

B

A

B

COMPOSITIONS AND METHODS FOR THE TREATMENT OF SJÖRGREN'S SYNDROME

CROSS-REFERENCE TO RELATED APPLICATIONS

This application claims the benefit under 35 U.S.C. §119 (e) of U.S. provisional application No. 61/301,535, filed Feb. 4, 2010, the entirety of which is hereby incorporated by reference into the present disclosure.

STATEMENT AS TO FEDERALLY SPONSORED RESEARCH OR DEVELOPMENT

This invention was made with government support under the Contract Nos. RO1 EY011386, EY017293 and EY016985 awarded by the National Institutes of Health. The government has certain rights to the invention.

FIELD OF THE INVENTION

This invention relates to compositions and methods for the treatment of the autoimmune disorder Sjögren's syndrome.

BACKGROUND

Sjögren's syndrome (SjS) is a chronic autoimmune inflammatory disease characterized by lymphocytic infiltration and destruction of lacrimal glands (LG) and salivary gland function (SG). SjS can occur independently (primary SjS) or in conjunction with another autoimmune disease (secondary SjS); both forms may progress to systemic disease of other organs. In both primary and secondary SjS, the presenting symptoms of ocular surface dryness, corneal irritation and increased susceptibility to infection overlap with symptoms of simple keratoconjunctivitis sicca (KCS).

The lacrimal gland (LG) produces most of the proteins present in the ocular surface fluid including growth factors, glycohydrolases, secretory immunoglobulin A, and other anti-infectives. Changes in tear quality and quantity can lead to keratoconjunctivitis sicca (KCS), or dry eye. KCS results from tear deficiency associated with altered LG function or from increased evaporative loss. The most serious cases of tear-deficient KCS are due to Sjogren's syndrome (SjS) and graft-versus-host disease (GVHD); these diseases are characterized by lymphocytic infiltrates in LG and salivary gland (SG) and production of autoantibodies associated with functional quiescence. A principal function of lacrimal gland acinar cells (LGAC) is regulated apical exocytosis of secretory vesicles (SV) containing tear proteins. Within LGAC, proteins destined for apical secretion via regulated exocytosis and proteins destined to function in the lysosomes (Lys) follow the same biosynthetic pathway through the endoplasmic reticulum (ER) and Golgi complex to the trans-Golgi network (TGN). The TGN is the cells' primary nexus for sorting intraluminal, fluid phase and membrane-embedded proteins. For the LG to sustain its primary secretory function, the TGN must sort proteins into the two pathways efficiently and accurately. TGN missorting of secretory proteins would markedly alter the nutrient and protective functions of the tear film. The fidelity of TGN sorting also becomes critical for Lys proteins because so many of these are proteases. If sorted improperly, Lys proteins may hydrolyze cellular autoantigens aberrantly and generate pathogenic epitopes; if they enter exocrine SV they may also damage other proteins being stored for secretion, and then when secreted, damage the cornea or conjunctiva. Evidence from SjS patients for such sorting defects occurring in the TGN of exocrine glands has been reported. While the molecular mechanisms in the LG that mediate the sorting and exocytosis of secretory proteins into tear fluid is yet to be elucidated and characterized, patients with severe SjS or GVDH still require effective therapies. This invention serves to satisfy this need and provide related advantages as well.

SUMMARY

This invention provides a method of inducing a lacrimal acinar cell in a tissue to degrade a secretory vesicle and its content protein or proteins from the trans-Golgi network (TGN) by contacting the cell with an effective amount of an agent that induces autophagy, thereby inducing the cell to degrade the secretory vesicle and its content protein or proteins from the trans-Golgi network. In one aspect the contacting is conducted in vitro. In another aspect, the contacting is conducted in vivo.

This invention provides a method of inhibiting the missorting of secretory protein or proteins by inducing a lacrimal acinar cell in a tissue to degrade a secretory vesicle and its content protein or proteins from the trans-Golgi network (TGN) comprising, or alternatively consisting essentially of, or yet further consisting of contacting the cell with an effective amount of an agent that induces autophagy, thereby inhibiting the missorting of a secretory protein or proteins from the trans-Golgi network. This method can be performed in appropriate tissue model in vitro or in a subject in vivo.

Also provided is a method, of treating a mammal suffering from one or more condition selected from an inflammatory autoimmune lacrimal gland disease, Graft versus Host Disease (GVHD) or primary or secondary Sjogren's Syndrome (SjS) comprising or alternatively consisting essentially of, or yet further consisting of administering to the mammal an effective amount of an agent that induces a lacrimal acinar cell in a tissue to degrade a secretory vesicle and its content protein or proteins from the trans-Golgi network (TGN), thereby treating the mammal.

This invention also provides a method for treating a mammal suffering from defective trans-Golgi network-secretory vesicle (TGN-SV) sorting, comprising, or alternatively consisting essentially of, or yet further consisting of, administering to the mammal an effective amount of an agent that induces autophagy in the tissue having the defective TGN-SV sorting, thereby treating the mammal. In one aspect, the proteins that are missorted or not degraded are CATS or APO-F.

DETAILED DESCRIPTION

Figure 1:
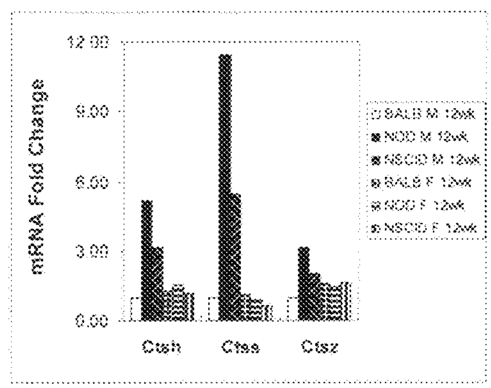
FIG. 1 depicts validation of microarray data and expanded investigation for genes of interest by real-time RT-PCR in LG from NOD, NOD SCID and BALB/c mice. Differentially expressed genes in LGs of NOD and BALB/c mice, suggested by microarray analysis, encoding Ctsh, Ctss, Ctsz and macrophage-produced cytokines were validated by real-time RT-PCR in LGs from 12-week-old NOD mice, matched BALB/c control, and more animal groups as shown in the figure panels. Certain relevant cytokines that were not detected by microarray due to its relative insensitivity were also re-evaluated in this study. Triplicates of each reaction were set up in parallel. The results were repeated 2-3 times and reproduced with RNAs from different batches of animals. The comparisons between different samples were conducted using the formulation of ΔΔCt study built into the ABI SDS 2.1 software. The expression level of all the genes in 12-week-old male BALB/c mice were designated as 1.0, and the expression levels of these genes in the rest of mice were compared to that in 12-week-old male BALB/c mice.
Figure 1:
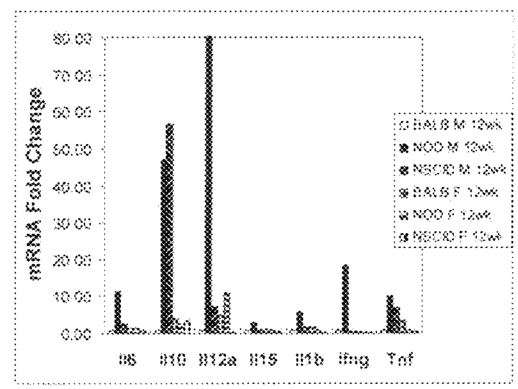
Figure 1:
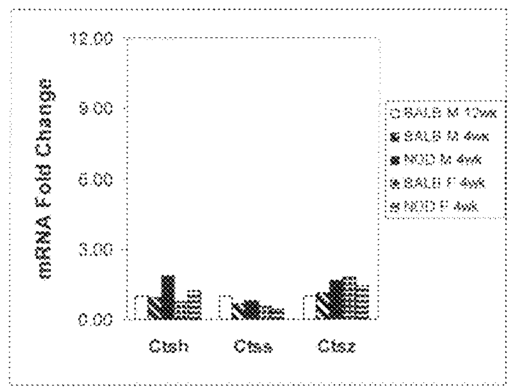
Figure 1:
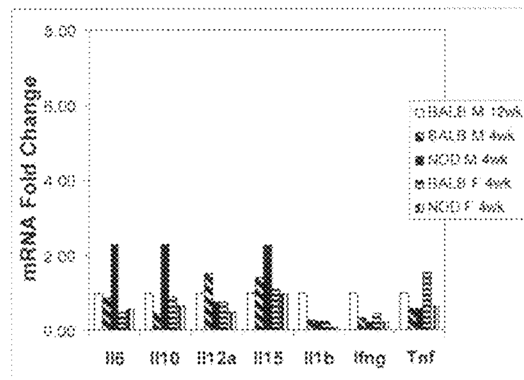

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, 3$^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney 5$^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLON- ING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

DEFINITIONS

As used herein, certain terms may have the following defined meanings. As used in the specification and claims, the singular form "a," "an" and "the" include singular and plural references unless the context dearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1" or alternatively a variation of the value of ±15%, or alternatively ±10%, or alternatively ±5%. It also is to be understood, although not always explicitly stated, that the reagents described herein are merely exemplary and that equivalents of such are known in the art.

The term "autophagy" or "autophagocytosis", as used herein refers to a catabolic process involving the degradation of a cell's own components through the lysosomal machinery. It is a tightly regulated process that plays a normal part in cell growth, development, and homeostasis, helping to maintain a balance between the synthesis, degradation, and subsequent recycling of cellular products. It is a major mechanism by which a starving cell reallocates nutrients from unnecessary processes to more essential processes. A variety of autophagic processes exist, all having in common the degradation of intracellular components via the lysosome.

As used herein, the term "mTOR" or "mechanistic target of rapamycin" refers to a protein having an amino acid sequence substantially identical to, or a mammalian protein homologue or isoform of, the human Beclin-1 sequence of GenBank Accession No. NP_004949. Suitable cDNA encoding Beclin-1 is provided at GenBank Accession No. 1.NM_004958. The protein encoded by this gene belongs to a family of phosphatidylinositol kinase-related kinases. These kinases mediate cellular responses to stresses such as DNA damage and nutrient deprivation.

The terms "protein", "polypeptide" and "peptide" are used interchangeably herein when referring to a gene expression product.

The term "recombinant protein" refers to a polypeptide which is produced by recombinant DNA techniques, wherein generally, DNA encoding the polypeptide is inserted into a suitable expression vector which is in turn used to transform a host cell to produce the protein.

A "mammal" is a class of vertebrate animals whose females are characterized by the possession of mammary glands while both males and females are characterized by sweat glands, hair, three middle ear bones' used in hearing, and a neocortex region in the brain. Non-limiting examples of a mammal include a simian, a lipoid, a murine, a bovine, an equine, a porcine or an ovine. In one aspect, a mammal is a mouse. In another aspect, a mammal is a rat. In yet another aspect, a mammal is a lepoid. In yet another aspect, a mammal is a human.

"Expression" as applied to a gene or a protein, refers to the production of the mRNA transcribed from the gene or the protein product encoded by the gene. In one aspect, "expression" level is determined by measuring the expression level of a gene of interest for a given population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest. Alternatively, the expression level of a gene is compared to the expression level of one or alternatively more than one patient with a desired genotype or phenotype, and then determined to be higher or lower or "overexpressed" or "underexpressed."

The phrase "biologically equivalent polypeptide" or "biologically equivalent peptide fragment" refers to protein, polynucleotide, or peptide fragment which hybridizes to the exemplified polynucleotide under stringent conditions and which exhibits similar biological activity e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence identity or homology. Percentage identity or homology can be determined by sequence comparison using programs such as BLAST run under appropriate conditions. In one aspect, the program is run under default parameters.

As understood by those of skill in the art, a "retro-inverso" refers to an isomer of a linear peptide in which the direction of the sequence is reversed ("retro") and the chirality of each amino acid residue is inverted ("inverso"). Compared to the parent peptide, a helical retro-inverso peptide can substantially retain the original spatial conformation of the side chains but has reversed peptide bonds, resulting in a retro-inverso isomer with a topology that closely resembles the parent peptide, since all peptide backbone hydrogen bond interactions are involved in maintaining the helical structure. See Jameson et al., (1994) Nature 368:744-746 (1994) and Brady et al. (1994) Nature 368: 692-693. The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

The term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" are used synonymously and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

The term "treating" as used herein is intended to encompass curing as well as ameliorating at least one symptom of the condition or disease.

"An effective amount" intends to indicate the amount of a compound or agent administered or delivered to the patient which is most likely to result in the desired treatment outcome. The amount is empirically determined by the patient's clinical parameters including, but not limited to the stage of disease, age, gender, histology, and likelihood for recurrence.

As used herein the term "inducing" intends to increase or augment as compared to a base level measured prior to treatment or contacting.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An agent of the present invention can be administered for therapy by any suitable route of administration. It will also be appreciated that the preferred route will vary with the condition and age of the recipient, and the disease being treated.

The agents and compositions of the present invention can be used in the manufacture of medicaments and for the treatment of humans and other animals by administration in accordance with conventional procedures, such as an active ingredient in pharmaceutical compositions.

"A "pro-autophagy" agent is one that induces or promotes autophagy.

The term "FLIP" is conventionally defined as a FLICE-like inhibitor protein having two death effector domains, DED1 and DED2. (Thome and Tschopp (2001) Nat. Rev. Immunol. 1:50-58). As used herein, the term "cFLIP" refers to the short and long form of cellular FLIP. cFLIPs refers to the short form of cFLIP. $cFLIP_L$ refers to the long form of cFLIP. The "viral" form of FLICE-like inhibitor protein refers to viral FLIP (vFLIP) any one of Kaposi's sarcoma-associated herpesvirus (KSHV), Herpesvirus saimiri (HVS), or Molluscum contagiosum virus (MCV). As used herein, "FLIP" refers cFLIP or vFLIP. Examples of FLIP peptides, proteins, conjugates and compositions containing them are described in U.S. Ser. No. 13/055,707, filed Jan. 24, 2011, incorporated herein by reference in its entirety.

"Sjögren's syndrome" or "SjS" affects an estimated 4 million Americans, with 9 out of 10 patients being women (Lemp (2005) Am. J. Ophthalmol. 140(5):898-9; Hansen et al. (2005) Curr. Opin. Rheumatol. 17(5):558-65). SjS is the second most common autoimmune disease in the United States; research into the improved diagnosis and treatment for these autoimmune disorders has long been recognized by the Office for Research on Women's Health (ORWH) as a priority. The lacrimal gland (LG) is responsible for secretion of proteins and fluid to sustain the health of the ocular surface (OS). SjS is characterized by lymphocytic infiltration of LG and salivary gland (SG), followed by development of functional quiescence (e.g., inability to secrete fluid and proteins) as well as the eventual inflammatory destruction of these glands. The ocular surface of SjS patients becomes desiccated and prone to infection because of the functional quiescence of the gland as well as changes in the spectrum of secreted proteins, leading to severe corneal damage and in some cases, blindness. SjS can occur independently (primary SjS) or in conjunction with another autoimmune disease such as rheumatoid arthritis or systemic lupus erythematosus (secondary SjS). Primary SjS in particular is associated with significant effects on other organs including the brain, kidneys, lungs, pancreas and gastrointestinal tract (Hansen et al. (2005) Curr. Opin. Rheumatol. 17(5):558-65)). A diagnosis of primary SjS is also associated with a significantly increased risk of B cell lymphoma. In primary and secondary SjS, the presenting symptoms overlap with other keratoconjunctivitis sicca (KCS) disorders while for secondary SjS, the presenting symptoms also overlap with many other autoimmune diseases. The SjS Foundation estimates that it requires nearly 7 years for the typical patient to receive a diagnosis of SjS, because the symptoms overlap so substantially with those for other diseases. Since the tears and saliva are thought to be uniquely altered in SjS, it is astounding that there are currently no tear or salivary biomarkers that are recognized as diagnostic for SjS, in particular for primary SjS, and which can aid in the early identification of this subset of SjS patients that will experience more severe disease. Since SjS, like most autoimmune diseases, is so strongly manifested in post-menopausal women relative to other populations, the success of this invention will also constitute a critical advance in diagnosis of a disease that has a tremendous impact on women's health.

Disease models for SjS include the NOD mouse and the IL-1-injected BALB/c mouse. They represent two models of inflammatory autoimmune LG disease. These two models differ in that one is a genetic model and the other is an experimentally-induced disease model which uses cytokine injection to induce LG disease.

"NOD mouse" is a well-studied genetic animal model for human insulin-dependent diabetes mellitus and SjS (Barabino et al. (2004) Invest. Ophthalmol. Vis. Sci. 45(6):1641-6). This strain spontaneously develops lymphocytic infiltration in submandibular glands (sialoadenitis) and LG (dacryoadenitis), and diabetes. Male NOD mice are significantly more susceptible to dacryoadenitis, and disease development in the female mouse LG is minimal. This differs from the human disease since SjS is more prevalent in women. Despite this difference, the lymphocytic infiltration into the LG of male mice is profound and occurs as early as 6 weeks, along with decreased production of tear fluid. The male NOD mouse LG also exhibits significant lipid deposition, a feature of human SjS. This genetic model system has been useful in generating strong leads for the protein biomarkers in tear fluid that are proposed to increase in disease: CtsS, Apo-F and Lcn-2. Male NOD mice, which develop the severe autoimmune inflammatory LG disease, will be utilized for tear fluid collection, in parallel with measurement of tear flow and corneal, conjunctival and LG integrity and inflammation. The ages of mice examined can span disease onset (4-12 weeks), intermediate development of disease (12 weeks-6-months) and advanced disease (6-12 months). Age- and gender-matched BALB/c mice can be used as controls.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

DESCRIPTIVE EMBODIMENTS

This invention provides a method of inducing a lacrimal acinar cell in a tissue to degrade a secretory vesicle and its content protein or proteins from the trans-Golgi network (TGN) by contacting the cell with an effective amount of an agent that induces autophagy, thereby inducing the cell to degrade the secretory vesicle and its content protein or proteins from the trans-Golgi network. In one aspect the contacting is conducted in vitro. In another aspect, the contacting is conducted in vivo.

This invention provides a method of inhibiting the missorting of a secretory protein or proteins by inducing a lacrimal acinar cell in a tissue to degrade a secretory vesicle and its content protein or proteins from the trans-Golgi network (TGN) comprising, or alternatively consisting essentially of, or yet further consisting of contacting the cell with an effective amount of an agent that induces autophagy, thereby inhibiting the missorting of secretory proteins inducing the cell in the tissue to degrade a secretory vesicle and its content protein or proteins from the trans-Golgi network. This method can be performed in appropriate tissue model in vitro or in a subject in vivo.

Also provided is a method of treating a mammal suffering from one or more condition selected from defective degradation of a secretory vesicle and its content proteins or protein, an inflammatory autoimmune lacrimal gland disease, Graft versus Host Disease (GVHD) or primary or secondary Sjogren's Syndrome (SjS) comprising or alternatively consisting essentially of, or yet further consisting of administering to the mammal an effective amount of an agent that induces a lacrimal acinar cell in a tissue to degrade a secretory vesicle and its content protein or proteins from the trans-Golgi network (TGN), thereby treating the mammal.

Also provided is a method for treating a mammal suffering from defective trans-Golgi network-secretory vesicle (TGN-SV) sorting, comprising, or alternatively consisting essentially of or yet further consisting of administering to the mammal an effective amount of an agent that induces autophagy in the tissue having the defective TGN-SV, thereby treating the mammal.

The protein or proteins that are missorted are identified herein. In one aspect, the defective TGN-SV sorting is the result of the mammal suffering from one or more of inflammatory autoimmune lacrimal gland disease, Graft versus Host Disease (GVHD) or primary or secondary Sjogren's Syndrome (SjS). Thus, by treating the defective TGN-SV sorting, the symptoms of these diseases are ameliorated or in some aspect the diseases are treated. Under appropriate conditions, a therapeutically effective amount is administered.

The above methods are useful for the treatments of mammals, e.g., a murine, a simian, a bovine, an ovine, a leporid, or a human patient. When the methods are practiced in vitro, the cells or tissue to be contacted are mammalian cells or tissues.

In one aspect, the treatment is successful when the symptoms of dry eye and/or tear loss is reduced or ameliorated.

For the above methods, the agent is administered locally or systemically.

Any agent believed to induce autophagy of the secretory vesicle and its content protein or proteins from the TGN can be used in the methods of this invention, an example of which is rapamycin. It is commercially available from LC Laboratories, Inc. Rapamycin is a macrolide compound obtained from *Streptomyces hygroscopicus* previously used as an immunosuppressant in tissue transplantation. Other reported autophagy-inducing compounds include verapamil and clonidine. Verapamil typically is prescribed for high blood pressure. It is an L-type calcium channel antagonist and stimulates autophagy by reducing the influx of calcium into cells. Clonidine is typically prescribed for migraines. It acts by regulating inositol trisphosphate ($IP_3$) levels. It induces autophagy through the reduction of cAMP or cyclic adenosine monophosphate.

Additional agents that have been shown to induce autophagy include isolated peptide fragments of vFLIP and cFLIP proteins that inhibit or diminish the ability of cFLIP or vFLIP to bind to Atg3 and inhibit formation of the LC3-Atg4-Atg7-Atg3 conjugation complex that is necessary for autophagy induction. The peptide fragments are useful therapeutically to augment or promote autophagy in a cell, tissue or subject. Biological active FLIP protein fragments are known in the art and described in Lee et al. (2009) Nature Cell Biology 11(11):1355.

Thus, in one aspect the methods of this invention are practiced by the administration of an isolated peptide fragment comprising, or alternatively consisting essentially of, or yet further consisting of, a pro-autophagy region of the vFLIP or cFLIP protein that binds to Atg3, or a portion thereof. In some aspects, the isolated peptide fragment comprises, or alternatively consists essentially of, or yet further consists of, a region of the death effector domain (DED) of vFLIP or cFLIP, or a portion thereof. See Bushell et al. (2008) Mol. Cell 30(3):262-263. In another aspect, the isolated peptide fragment comprises, or alternatively consists essentially of, or yet further consists of, an alpha-helix region of a DED of vFLIP or cFLIP, or a portion thereof.

An additional example includes an isolated peptide fragment of vFLIP comprising, or alternatively consisting essentially of, or yet further consisting of, the amino acid sequence EVVLFLLNVF (SEQ ID NO. 1) or a peptide fragment substantially homologous and biologically equivalent to SEQ ID NO. 1 or alternatively the retro-inverso form. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 1, each as determined using methods known to those skilled in the art and identified herein, when run under default parameters.

An additional example includes an isolated peptide fragment of vFLIP that comprises, or alternatively consists essentially of, or yet further consists of, the amino acid sequence QTFLHWVYCMEN (SEQ ID NO. 2) or a peptide fragment substantially homologous and biologically equivalent to SEQ ID NO. 2 or alternatively the retro-inverso form of these peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 2, each as determined using methods known to those skilled in the art and identified herein, when run under default parameters.

In yet another aspect an additional example includes an isolated peptide fragment of vFLIP that comprises, or alternatively consists essentially of, or yet further consists of, the amino acid sequence EMLLFLCRDV (SEQ ID NO. 3) or a peptide fragment substantially homologous and biologically equivalent to SEQ ID NO. 3 or alternatively, the retro-inverso forms of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 3, each as determined using methods known to those skilled in the art and identified herein, when run under default parameters.

In still another aspect this invention, the methods are practiced with an isolated peptide fragment of cFLIP comprising, or alternatively consisting essentially of, or yet further consisting of, the amino acid sequence KSFLDLVVELEK (SEQ ID NO. 4) or a peptide fragment substantially homologous and biologically equivalent to SEQ ID NO. 4 or alternatively the retro-inverso forms of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 4, each as determined using methods known to those skilled in the art and identified herein, when run under default parameters.

In another aspect this invention the methods are practiced with an isolated peptide fragment of HVS vFLIP that comprises, or alternatively consists essentially of, or yet further consists of, the amino acid sequence YCLLFLINGC (SEQ ID NO. 5) or a peptide fragment substantially homologous and biologically equivalent to SEQ ID NO. 5 or alternatively the retro-inverso forms of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 5, each as determined using methods known to those skilled in the art and identified herein, when run under default parameters.

The methods can also be practiced with an isolated peptide fragment of HVS vFLIP that comprises, or alternatively consists essentially of, or yet further consists of, the amino acid sequence SSVILCVFSNMLC (SEQ ID NO. 6) or a peptide fragment substantially homologous and biologically equivalent to SEQ ID NO. 6, or alternatively, the retro-inverso forms of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 6, each as determined using methods known to those skilled in the art and identified herein, when run under default parameters.

In another aspect, the methods can be practices by an isolated peptide, fragment of MCV MC159 comprising, or alternatively consisting essentially of, or yet further consisting of, the amino acid sequence SLLLFLCHDA (SEQ ID NO. 7) or a peptide fragment substantially homologous and biologically equivalent to SEQ ID NO. 7 or alternatively, the retro-inverso forms of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 7, each as determined using methods known to those skilled in the art and identified herein, when run under default parameters.

In another aspect this invention, the methods are practiced with an isolated peptide fragment of MCV MC159 comprising, or alternatively consisting essentially of, or yet further consisting of, the amino acid sequence SRFVELVLALEN (SEQ ID NO. 8) or a peptide fragment substantially homologous and biologically equivalent to SEQ ID NO. 8 or alternatively, a retro-inverso forms of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 8, each as determined using methods known to those skilled in the art and identified herein, when run under default parameters.

The peptides can be administered as peptides or as polynucleotides encoding the peptides with the appropriate expression elements operably linked to the sequence encoding the peptide fragments.

This invention also provides a formulation for use in the above methods. The formulation comprises, or alternatively consists essentially of, or yet further consists of an effective amount of an pro-autophagy inducing agent and a carrier. In one aspect, the carrier is a pharmaceutically acceptable carrier that is appropriate for topical administration to the tear ducts or eyes.

Further provided is the use of a pro-autophagy agent to prepare a medicament that induces a lacrimal acinar cell in a tissue to degrade a secretory vesicle and its content protein or proteins from the trans-Golgi network (TGN). This invention also provides the use of a pro-autophagy agent to prepare a medicament to treat a patient suffering from defective trans-Golgi network-secretory vesicle (TGN-SV) sorting or defective degradation of a secretory vesicle and its content protein or proteins. Still further provided is the use of a pro-autophagy agent to prepare a medicament to treat one or more of an inflammatory autoimmune lacrimal gland disease, Graft versus Host Disease (GVHD) or primary or secondary Sjogren's Syndrome (SjS). The medicaments comprise, or alternatively consist essentially of, or yet further consist of an effective amount of an pro-autophagy inducing agent and a carrier. In one aspect, the carrier is a pharmaceutically acceptable carrier that is appropriate for topical administration to the tear ducts or eyes.

Any agent believed to induce autophagy can be used in the medicaments of this invention, an example of which is rapamycin. It is commercially available from LC Laboratories, Inc. Rapamycin is a macrolide compound obtained from *Streptomyces hygroscopicus* previously used as an immunosuppressant in tissue transplantation. Other reported autophagy-inducing compounds include verapamil and clonidine.

This invention also provides a method to identify agents that will inhibit the missorting of secretory proteins by inducing lacrimal acinar cells in a tissue to degrade secretory vesicles and their contents from the trans-Golgi network (TGN) and/or treating a mammal suffering from defective trans-Golgi network-secretory vesicle (TGN-SV) sorting and/or treating a mammal suffering from one or more of inflammatory autoimmune lacrimal gland disease, Graft versus Host Disease (GVHD) or primary or secondary Sjogren's Syndrome (SjS). In one aspect, the agent to be tested or screened is contacted with a tissue containing lacrimal acinar cells under conditions that will induce autophagy of the secretory vesicles in the tissue. Agents that promote degradation are identified as potential therapeutics that can be further tested in the animal models disclosed herein. Alternatively, after administration of the test agent, the biomarkers for the disease (as identified herein) can be assayed for. Agents that prevent or inhibit missorting of proteins are agents that can be used in the methods of this invention. One or more of Rapamycin verapamil and/or clonidine can be tested simultaneously as a positive control.

Experimental

The lacrimal gland (LG) produces most of the proteins present in the ocular surface fluid including growth factors, glycohydrolases, secretory immunoglobulin A, and other anti-infectives. Changes in tear quality and quantity can lead to keratoconjunctivitis sicca (KCS), or dry eye. KCS results from tear deficiency associated with altered LG function or from increased evaporative loss. The most serious cases of tear-deficient KCS are due to Sjögren's syndrome (SjS) and graft-versus-host disease (GVHD); these diseases are characterized by lymphocytic infiltrates in LG and salivary gland (SG) and production of autoantibodies associated with functional quiescence. A principal function of lacrimal gland acinar cells (LGAC) is regulated apical exocytosis of secretory vesicles (SV) containing tear proteins. Within LGAC, proteins destined for apical secretion via regulated exocytosis and proteins destined to function in the lysosomes (Lys) follow the same biosynthetic pathway through the endoplasmic reticulum (ER) and Golgi complex to the trans-Golgi network (TGN). The TGN is the cells' primary nexus for sorting intraluminal, fluid phase and membrane-embedded proteins. For the LG to sustain its primary secretory function, the TGN must sort proteins into the two pathways efficiently and accurately. TGN missorting of secretory proteins would markedly alter the nutrient and protective functions of the tear film. The fidelity of TGN sorting also becomes critical for Lys proteins because so many of these are proteases. If sorted improperly, Lys proteins may hydrolyze cellular autoantigens aberrantly and generate pathogenic epitopes; if they enter exocrine SV they may also damage other proteins being stored for secretion, and then when secreted, damage the cornea or conjunctiva. Evidence from SjS patients for such sorting defects occurring in the TGN of exocrine glands has been reported.

Loss of critical secretory proteins from SV of LGAC due to defective TGN-SV sorting may mimic aspects of functional quiescence by adversely affecting the function of the tear film and by resulting in efflux of missorted secretory proteins through membrane compartments such as Lys. Without being bound by theory, Applicants hypothesize that disruption of TGN-to-SV sorting alters Lys organization, contents and thus ocular surface integrity. Cellular responses to authophagy inducing agents can be tested in LG from a mouse model with a defined TGN-SV sorting defect, and in cultured LGAC in which TGN-SV sorting has been modified, using rigorous biochemical approaches in parallel with confocal fluorescence microscopy (CFM) and electron microscopy (EM). The consequences to the ocular surface of abnormal TGN-SV trafficking can also be analyzed in mouse models using classical approaches (fluorescein staining, histology) in parallel with second harmonic generation (SHG) imaging and optical coherence tomography (OCT) analysis of the ocular surface.

The male NOD mouse, a model of SjS, exhibits missorting of the Lys protease Cathepsin S (CtsS) into LG SV in parallel with damage to the corneal stroma. Without being bound by theory, Applicants hypothesize that missorting from TGN-Lys elicits pathological changes in the composition and content of SV which lead to ocular surface damage. Autophagy inducing agents and cellular responses to TGN-Lys sorting defects can be tested as described herein in a mouse model with an established TGN-Lys sorting defect and in cultured LGAC in which the pathways have been modified. The consequences of the predicted increased flow of Lys proteins to ocular surface integrity in mouse models will be analyzed as described above.

Autophagy is a physiological response to starvation, high bioenergetic demand or ER stress. Induction of autophagy has been linked to recovery of the LG from cytokine-induced inflammatory autoimmune disease. Diseased LG from male NOD mice exhibit ER stress, impaired biosynthetic trafficking, but no autophagy. Without being bound by theory, Applicants hypothesize that induction of autophagy reverses some of the pathological changes associated with TGN missorting in the male NOD mouse. Autophagy can be induced in this model and analyzed whether normal membrane trafficking and healthy ocular surface function can be restored, as described above.

Use of the Male NOD Mouse

The male NOD mouse is a well-established animal model in which to evaluate the processes of dacryoadenitis and sialoadenitis characteristic of the human disease. This mouse strain spontaneously develops insulin-dependent diabetes mellitus (IDDM) as well as SjS-like disease. Dacryoadenitis, which is more severe than sialoadenitis in this mouse model, is fully-manifested by 12-16 weeks. The manifestations and pathological characteristics of the affected LG in the NOD mouse resemble those changes seen in LG of patients suffering from dacryoadenitis of Sjögren's syndrome. The NOD SCID mouse strain is an immune-incompetent NOD mouse. Prkdc congenic strain can be compared to the NOD mouse to distinguish events associated with inflammation versus events characteristic of the strain that are independent of T- and B-cell mediated inflammatory responses. The NOD SCID strain lacks functional T, B and NK cells, and is free of exocrine tissue destruction.

The early pathological events associated with dacryoadenitis in the NOD mouse and other disease models include the development of functional quiescence (e.g., inability of acinar cells to secrete tear proteins from pre-formed secretory vesicles) in LG regions with otherwise normally-appearing and intact acinar cells, the infiltration of inflammatory cells from ducts into other regions of the LG to form foci, and the damage of extracellular matrix and other acinar cells by factors released from these infiltrating immune cells. Over time, the healthy acinar cell mass in the LG is replaced by lymphocytic foci and regions of necrotic and apoptotic cell debris. Some of the early functional change in otherwise normally-appearing acini have also been linked to exposure to inflammatory cytokines. For instance, it has been shown that IL1$\alpha$ and IL1$\beta$, constituents of the inflammatory cytokine milieu, can elicit functional changes in release of neurotransmitters from innervating nerves with the LG responsible for modulation of secretory responses, and may also elicit direct functional quiescence when exposed to acinar cells in vitro. However the factors responsible for triggering the initial autoimmune inflammatory response that contribute to elevated cytokine levels in the LG and then progress to elicit this cycle of damage are still poorly understood.

The Balb/c mouse can also be used as an experimental model. Because this model is induced, Applicants can track disease development, progression and recovery in the female, which more accurately represents the SjS disease demographic in this capacity relative to the NOD model. BALB/c mice recover more quickly from the cytokine injection, within a week, while C57BL/6 mice display a more gradual recovery of within a few weeks. For injection of female mice, aged 10-12 weeks with IL-1, recombinant human IL-1$\alpha$ can be used. Both IL-1$\alpha$ and IL-1$\beta$ elicit comparable effects in the LG disease model but it is anticipated that it may be possible to secure some IL-1$\alpha$ from the NCI Preclinical Repository to supplement the studies. LG in anesthetized mice will be injected with IL-1$\alpha$ (1 μg) to in 2 μL into each LG. Controls will be injected with comparable volumes of saline. Tear fluid collection, tear flow, and corneal, conjunctival and LG integrity and inflammation will be assessed in mice from 1-10 days post-injection.

Animals and animal procedures: The NOD and BALB/c mouse colonies can be bred in the University of Southern California Vivarium using breeding pairs purchased from Taconic (Hudson, N.Y.) and/or Charles River Laboratories (Wilmington, Mass.). NOD SCID mice were purchased from Harlan (Indianapolis, Ind.). Animals can be treated and sacrificed in accordance with policies approved by the University of Southern California Institutional Animal Care and Use Committee. The LG can be removed from mice at different ages, after the animals are euthanized by intraperitoneal injection with 55 mg of Ketaject and 14 mg of Xylazine per kg of body weight followed by cervical dislocation. After being removed, LG are either snap frozen and stored in liquid nitrogen for RNA preparation, or fixed immediately with 4% paraformaldehyde and 4% sucrose in PBS for processing and analysis using indirect immunofluorescence.

Reagents and supplies: The VersaGene RNA Tissue Kit, originally from Gentra Systems, purchased from Thermo Fisher Scientific, Inc. (Fair Lawn, N.J.) under the name 5 PRIME PerfectPure RNA Tissue Kit (FP2302410). All materials and reagents for microarray can be purchased from Applied Biosystems (ABI, Foster City, Calif.) through the Vanderbilt Microarray Shared Resources (VMSR, Vanderbilt University, Nashville, Tenn.). All the following materials and reagents for RT and real-time PCR can be purchased directly from ABI: the high capacity cDNA RT kit (4368814), TaqMan® universal PCR master mix for real-time PCR (4324018), MicroAmp™ optical 384-well reaction plates (4309849) and MicroAmp™ optical adhesive films (4311971), and TaqMane gene expression assays (groups 1 and 2). Group 1 probes include those for the genes of interest including I11b (Mm01336189_m1 or Mm00434228_m1), I16 (Mm_m1), I110 (Mm_m1), I115 (Mm00434210_m1), Tnfa (Mm_m1), Infg (Mm_m1), Ctsh (Mm00514455_m1) Ctss (Mm00457902_m1) and Ctsz (Mm00517697_m1). Group 2 probes include those for genes serving as internal controls including Hprt1 (Mm00446968_m1) and Sdha (Mm01352357_m1). Mm followed by 8 digits represents the company assay ID for a TaqMan gene expression assay corresponding to a specific mRNA locus of a gene.

Rat anti-cathepsin H (CATH) monoclonal antibody (MAB1013) and Goat anti-cathepsin S (CATS) polyclonal antibody (3366-100) for Western blotting can be purchased from R&D Systems, Inc. (Minneapolis, Minn.) and BioVision, Inc. (Mountain View, Calif.) respectively; goat anti-CATH polyclonal antibody (sc-6497), goat, anti-CATS polyclonal antibody (sc-6505), and rat anti-mouse CD14 monoclonal antibody (sc-9150) used for immunofluorescent microscopy can be purchased from Santa Cruz Biotechnology, Inc. (Santa Cruz, Calif.). Rat anti-Lamp2 monoclonal antibody (ab13524) from Abcam USA (Cambridge, Mass.); rat anti-CD68 monoclonal antibody (MCA1957GA) from AbD Serotec USA (Raleigh, N.C.); and Rhodamine Red-X-conjugated donkey anti-goat IgG (705-295-147), FITC-conjugated donkey anti-goat IgG (711-095-152) and FITC-conjugated donkey anti-rat IgG (712-095-150) from Jackson ImmunoResearch Laboratories (West Grove, Pa.) can be used for immunofluorescence analysis. Raw264.7 whole cell lysate can be used as the positive control for CATH and CATS proteins analyzed by Western blotting and can be purchased from Santa Cruz Biotechnology, Inc. (Santa Cruz Calif., USA). Carbamylcholine (CCH) can be purchased from Sigma (St. Louis, Mo., USA).

Fluorescence-activated cell sorter (FACS) analysis: FACS analysis can be performed on inflammatory cells that were isolated from LG of 12 week old BALB/c, NOD and NOD SCID mice (n=5 mice, pooled) according to a modified protocol as described previously (Schenke-Layland et al., 2008). Inflammatory cell subsets can be dual-labeled with the following antibodies: fluorescein isothiocyanate (FITC)-conjugated CD49b/Pan-NK; cyanine-5 (Cy5)-conjugated CD11b (Mac-1) and phycoerythrin (PE)-conjugated Gr1; PE-conjugated B220 and FITC-conjugated CD19; as well as FITC-conjugated CD4 and PE-conjugated CD8. All these antibodies can be purchased from BD Biosciences/Pharmingen (San Diego, Calif., USA) and used according to the manufacturer's protocol. Nonspecific isotype-matched Cy5-, PE- and FITC-conjugated IgGs can serve as controls. Staining with 7-amino-actinomycin (7-AAD; BD Pharmingen, San Diego Calif., USA) can be performed to exclude dead cells according to the manufacturer's instructions. Cells are gated properly and a total of 10,000 events can be acquired for each sample. All analyses are performed using a BD LSR2 flow cytometer (BD Bioscience, San Jose, Calif., USA). FACS files can be exported and analyzed using the FlowJo 8.3.3 software (Tree Star Inc., Ashland, Oreg., USA).

Preparation of total RNA: The preparation can be conducted using the VersaGene RNA Tissue Kit or 5 PRIME PerfectPure RNA Tissue Kit at room temperature. One to two pairs of LG can be taken out from liquid nitrogen, and quickly homogenized on ice using a Brinkman Polytron tissue homogenizer in lysis buffer. The lysate can be filtered through a Pre-Clear spin column by centrifugation. The clarified lysate can be passed through a purification column by centrifugation. The RNA-bound membrane can be treated with DNase I. The RNA can be eluted into a collection tube from the column with elution buffer. Three LG RNA samples can be pooled from 3 mice in equal amounts for microarray analysis and real-time RT-PCR. Each RNA sample can be prepared for real-time RT-PCR from 3-4 pairs of pooled LG when 4-week-old mice can be used. All the purified RNA samples can be stored at −80° C.

Gene expression microarray analysis: Triplicates of ABI Mouse Genome Survey Microarray, AB1700 version 1.0.1 (4382672) can be used for each group of mice. Each chip can be printed with about 33,000 60-mer oligos as probes, representing a complete annotated and curated set of approximately 32,000 mouse genes from the public and Celera databases. The microarray analysis and the sequential data normalization can be conducted by VMSR. Before microarray, the purity and integrity of RNAs can be confirmed by measurement on an Agilent Bioanalyzer according to manufacturer's manual. In brief, 1 μg of total RNA (about 30 ng mRNA) can be used to generate double-stranded cDNA using ABI NanoAmp™ RT-IVT labeling kit (4365715) according to manufacturer's protocol. The entire cDNA product can be used in an IVT reaction to generate digoxigenin (DIG)-labeled cRNA. The cRNA can be purified using alit column and assessed for quality on an Agilent Bioanalyzer. All hybridization reagents, hybridization controls, wash reagents, and chemiluminescent reagents can be provided in the ABI Chemiluminescence Detection Kit (4342142), and the manufacturer's protocol can be followed in the subsequent hybridization procedure. Briefly, the arrays can be pre-hybridized with a 1 ml of pre-hybridization mixture for 60 min with agitation at 100 RPM and 55° C. in a hybridization oven. 0.5 ml of fragmented DIG-labeled targets mixed with hybridization controls can be added to the pre-hybridization solution. The arrays are continually incubated at 55° C. and agitated at 100 RPM for 16 hr. The arrays are washed and incubated with anti-DIG-AP antibody for 20 min. Following antibody washes, the arrays are incubated with Chemiluminescence Enhancing Solution for 20 min. Substrate for the chemiluminescence reaction can be added to each array individually one array at a time. The array can be immediately imaged on the 1700 Chemiluminescent Microarray Analyzer. The images can be assessed for QA/QC and a primary analysis can be completed by the AB1700 Expression Array System Software (v 1.1.1). The raw data can be normalized using the ABI quantile-based method and filtered according to the average scores of flags with the analyzer and associated software.

Reverse transcription (RT) and real-time polymerase chain reaction (PCR): Two reaction steps can be carried out with ABI reaction kits and reagents according to the manufacturer's protocols. Briefly, RT reaction can be conducted with 1 μg of RNA per 10 μl of reaction volume at 25° C. for 10 min then 37° C. for 2 hr, and terminated at 85° C. for 5 sec, using the high capacity cDNA RT kit. Real-time PCR can be conducted using an ABI 7900HT Fast Real-Time PCR System. 1 μl of RT product (diluted with 3.5 μl of nuclease-free $H_2O$), 0.5 μl of the TaqMan Assay Mixture and 5 μl of Universal Master Mix can be used in each PCR reaction in a total volume of 10 μl. Triplicates can be run for each assay. The samples are preheated at 95° C. for 10 min, followed by 40 cycles of 95° C. for 15 sec and 60° C. for 1 min. The PCR reaction with the TaqMan assay for the house-keeping genes, Hprt1 (hypoxanthine phosphoribosyltransferase 1) or Sdha (succinate dehydrogenase complex, subunit A), can be run as internal controls. The recorded data can be analyzed using the ΔΔCt study calculating function of the ABI software SDS 2.1. The fold change (FC) for a specific mRNA can be obtained by calculations as ΔCt=Ct (studied mRNA)−Ct (house keeping gene mRNA), ΔCt (NOD)−ΔCt (BALB/c)=ΔΔCt, and FC (NOD/BALB/c)=$2^{\Delta\Delta Ct}$.

Confocal fluorescence microscopy: After removal, LG can be incubated in PBS containing 4% paraformaldehyde and 4% sucrose at room temperature for 2-3 hr. The gland can be transferred to PBS containing 30% sucrose overnight. The glands can be embedded into O.C.T. and snap frozen in liquid nitrogen. The blocks can be stored at −80° C. prior to tissue sectioning. The blocks can be sectioned with a Microm Cryostat (Heidelberg, Germany) into 5 micron thick sections. The slides can be incubated with diluted primary antibody in 1% BSA on the top of the tissue section at 37° C. for 1 hr in a moisturized chamber. Sequentially diluted fluorophore-labeled secondary antibodies in 1% BSA and fluorophore-labeled phalloidin (where appropriate) can be applied and slides can be incubated in the moisturized chamber at 37° C. for 1 hr. Finally, slides can be incubated with DAPI in PBS for 5 min, rinsed with water and mounted with water soluble anti-fade mounting medium (Invitrogen, Carlsbad, Calif.) under a cover slip. During the whole procedure, slides can be washed with PBS 2-3 times between the treatments. Samples can be imaged with a Zeiss LSM 510 Meta NLO confocal/multiphoton imaging system.

Western blotting with LG tissue lysate or tear fluid: Pooled LGs can be removed from 2-3 mice freshly or stored at −80° C. were homogenized with a motor-driven homogenizer in RIPA buffer (150 mM NaCl, 50 mM Tris-Cl, 0.5% sodium deoxycholate, 0.5 mM EDTA, 0.1% TX-100, 1% NP-40) containing protease inhibitors in a tissue: buffer ratio of 1:5 (w/v). The resulting homogenate can be clarified by centrifugation at 10,000 rpm at 4° C. for 10 min. The supernatant can be collected and stored at −80° C. An aliquot of the supernatant can be mixed with SDS gel loading buffer and heated at 92° C. for 5 min for the subsequent analysis.

For tear collection, the mouse can be anesthetized as described above. The mouse LG can be exposed by a small incision along an axis defined by the outer junction of the eyelid and the ear, then covered with a layer of fine cellulose mesh (Kimwipe®) cut into a similar size as the gland. The LG can be stimulated by adding the agonist carbamylcholine (CCH) (5 μL, 10 μM) onto the mesh on the top of the gland, and tear fluid can be collected with glass capillaries at the medial canthus of the eye with care taken not to touch the cornea. Each eye can be stimulated two times, in a total collection time of 10 min per eye. The collected tear fluid can be transferred from the capillaries to an Eppendorf tube containing protease inhibitors, measured for precise volume, mixed with SDS gel loading buffer, pooled when necessary, and heated at 92° C. for 5 min.

Tissue lysate containing 100 μg of total proteins or 1 μl of tear fluid can be loaded to each well and resolved on 10-12% SDS PAGE. The membranes can be scanned using a LI-COR Odyssey Infrared Imaging System.

Measurement of enzymatic activity of cathepsins: For activity measurements in LG lysate, freshly collected LG pairs from each individual mouse, either post-stimulation after topical CCH for tear collection or without stimulation, can be homogenized with Brinkman Polytron tissue homogenizer on ice in CS Cell Lysis Buffer (1 mg tissue/5 μl buffer) provided in the Cathepsin S Activity Assay Kit (Biovision, Inc. Mountain View, Calif.). The same number of NOD and BALB/c mice can be used in each experiment. The homogenate can be clarified by centrifugation at 10,000×g, 4° C. for 10 min. The resulting lysate can be either used immediately or stored at −80° C. for later use.

For activity measurements in tears, mice can be anesthetized as described and tear fluid can be collected from paired 12-week-old male NOD and BALB/c mice, matched into pairs according to age and sex. The mice are placed resting on their sides under a Motic SMZ-140 dissection microscope (Xiamen, China). The LG can be exposed by a small incision along an axis defined bye the outer junction of the eyelid and the ear and connective tissue capsule enclosing the gland can be carefully opened and removed from the upper surface of the gland to which a layer of fine cellulose mesh (Kimwipe®) cut into the shape of the gland but slightly smaller can be applied. The ocular surface can be washed with AK-Rinse Eye Irrigating Solution (Akorn, Abita Spring, La.). The LG can be stimulated by adding the agonist CCH (3 μL, 50 μM) topically to the gland and tear fluid can be collected by carefully applying a 2 μL microcaps pipette, (Drummond, Broomall, Pa.) at the medial canthus of the eye, for 5 min. Care should be taken not to touch the cornea. Each eye can be stimulated with CCH three times, resulting in a total collection time of 15 min per eye. The microcaps can be emptied into sterile vials by the aspirator supplied by the manufacturer. The tears collected from both eyes of the same mouse are pooled and immediately analyzed for CATS activity.

CATS activity in LG lysate and tear fluid samples can be analyzed using the Cathepsin S Activity Assay Kit. The collected tear fluid of whole volume from each mouse or 10 μg of LG lysate is diluted to constitute the reaction mixture of 100 μL with or without inhibitor according to the manufacturer's instructions. The reaction is incubated at 37° C. for 1, 2, and 18 hr. The concentration of resulting fluorescent products can be measured using a fluorimeter with 505 nm emission filter. CATH activity can be assayed with the Cathepsin H Activity Assay Kit (BioVision, Inc.). The procedure can be similar to that for CATS activity assay except that only LG homogenate and not tears is analyzed in this assay.

Gene expression profiles of cathepsin family members and other inflammatory factors in LGs of NOD and BALB/c mice. Severe extracellular matrix degradation and immune cell infiltration are prominent features of LGs in male NOD mouse LG aged 12-18 weeks. Cathepsins are a major category of proteases responsible for regulation of extracellular matrix; in fact one of their roles as tear secretory proteins is to regulate extracellular matrix homeostasis. Gene expression profiles were analyzed to determine possible alterations in their expression in male NOD mouse LG, using gene expression microarray analysis to investigate if cathepsin family members contributed to these pathologic events associated with immune cell infiltration. The results are presented in Table 1. The hybridization signals for mRNAs of cathepsins H (Ctsh), R (Ctsr), S (Ctss), W (Ctsw), and Z (Ctsz) were elevated in the LG of NOD mice compared to the BALB/c controls. There was no difference for the rest of the cathepsin family members except cathepsin K (Ctsk) which showed expression that was 40% as high as the BALB/c control.

Macrophage-expressed cytokines and their receptors were also examined for their mRNA levels in the LGs of NOD mice relative to the BALB/c controls. However, only a subset of these cytokines and receptors were detected by microarray due to the relative insensitivity of this technique to low abundance mRNAs as shown in Table 2. The mRNA levels of interferon-γ, interleukin-10 receptor α and tumor necrosis factor α were clearly also higher in the LGs of male NOD mice than that of matched BALB/c mice.

Data validation and expanded investigation of gene expression. The results of microarray were validated by real-time RT-PCR which evaluated the expression levels of cathepsin family members and cytokines of interest. Beside the total RNAs from the LGs of 12-week-old male NOD and BALB/c mice, total RNAs from age matched NOD SCID mice.

TABLE 1

Differentially expressed cathepsin family members in LGs of NOD mice versus BALB/c mice characterized by microarray analysis

| Gene | NCBI Accession | FC (NOD/BALB) | P Value | Change in NOD |
|---|---|---|---|---|
| Ctsb | BC006656 | 1.0 | 0.3330 | no change |
| Ctsc | NM_009982 | 1.2 | 0.0624 | no change |
| Ctsd | NM_009983 | 1.0 | 0.3311 | no change |
| Ctsf | NM_019861 | 0.7 | 0.0006 | no change |
| Ctsh | NM_007801 | 2.1 | 0.0015 | increase |
| Ctsk | NM_007802 | 0.4 | 0.1128 | may decrease |
| Ctsl | NM_009984 | 0.9 | 0.4897 | no change |
| Ctso | NM_177662 | 1.4 | 0.1111 | no change |
| Ctsr | NM_020284 | 6.9 | 0.0015 | increase |
| Ctss | NM_021281 | 4.4 | 1.7E−07 | increase |
| Ctsw | NM_009985 | 3.1 | 0.0230 | increase |
| Ctsz | NM_022325 | 1.8 | 0.0029 | may increase |

FC represents the fold change obtained by comparing the hybridization signal of NOD mouse LG to the signal from BALB/c mouse LG (NOD/BALB/c) after normalization. The full names for the gene symbols listed in this table are: Cts(letter), genes for cathepsin family members.

TABLE 2

Increased mRNA levels of cytokines and proinflammatory factors in LG from NOD versus BALB/c mice characterized by microarray analysis

| Gene | NCBI Accession | FC (NOD/BALB) | P Value | Change in NOD |
|---|---|---|---|---|
| Ifng | NM_008337 | 14.5 | 1.2E−06 | increase |
| Il1b | NM_00836 | 1.3- | — | under detection |
| Il6 | NM_031168.1 | — | — | under detection |
| Il6ra | NM_010559 | 2.6 | 0.1740 | may increase |
| Il10 | NM_010548 | 2.6 | 0.0636 | may increase |
| Il10ra | NM_008348 | 6.1 | 0.0014 | increase |
| Il15 | NM_008357 | 1.8 | 0.3883 | may increase |
| Tnfa | NM_013693 | 4.6 | 0.0003 | increase |

FC represents the fold change obtained by comparing the hybridization signal of NOD mice to the signal of BALB/c mice (NOD/BALB/c) after normalization.

TABLE 3

Validation of microarray data of cathepsins by real-time RT PCR

| | Ctsh | Ctss | Ctsz |
|---|---|---|---|
| 12 wk Group | | | |
| BALB/c M | 1.0 ± 0 | 1.0 ± 0 | 1.0 ± 0 |
| NOD M | 8.2 ± 2.5*** | 9.3 ± 1.7*** | 2.3 ± 0.5** |
| NOD SCID M | 2.8 ± 1.0*** | 2.5 ± 1.2** | 1.6 ± 0.4** |
| BALB/c F | 1.0 ± 0.2 | 1.6 ± 0.4 | 1.5 ± 0.2 |
| NOD F | 1.4 ± 0.2 | 1.2 ± 0.3 | 1.5 ± 0.3 |
| NOD SCID F | 1.5 ± 0.7 | 1.0 ± 0.2 | 1.4 ± 0.1 |
| 4 wk Group | | | |
| BALB/c M | 1.0 ± 0 | 1.0 ± 0 | 1.0 ± 0 |
| NOD M | 1.6 ± 0.3* | 1.5 ± 0.2* | 1.4 ± 0.1** |
| BALB/c F | 0.8 ± 0.1 | 1.2 ± 0.2 | 1.3 ± 0.2 |
| NOD F | 1.2 ± 0.2 | 0.7 ± 0.1 | 1.4 ± 0.2 |

***P value < 0.001;

**P value < 0.01;

*P value < 0.05.

Each value depicts the average of 3-9 PCR results followed by ± standard deviation (SD). Each PCR result was obtained using an individual RNA sample prepared from pooled LG of three to four mice.

TABLE 4

Validation of microarray data of cytokines by real-time RT PCR

| | Il1b | Il6 | Il10 | Il12a | Il15 | Ifng | Tnf |
|---|---|---|---|---|---|---|---|
| 12 wk Group | | | | | | | |
| BALB/c M | 1.0 ± 0 | 1.0 ± 0 | 1.0 ± 0 | 1.0 ± 0 | 1.0 ± 0 | 1.0 ± 0 | 1.0 ± 0 |
| NOD M | 6.4 ± 0.6*** | 10.9 ± 2.8*** | 40.6 ± 10.4** | 497.2 ± 79.1** | 2.6 ± 0.2*** | 42.5 ± 26.4 | 12.0 ± 2.9** |
| NOD SCID M | 1.6 ± 0.8 | 2.2 ± 0.7*** | 2.3 ± 0.6* | ND | 1.0 ± 0.2 | 0.7 ± 0.1 | 3.4 ± 3.1 |
| BALB/c F | 2.0 ± 0.1 | 1.6 ± 0.6 | 2.3 ± 1.5 | 2.8 ± 1.9 | 1.5 ± 0.2 | 1.9 ± 1.7 | 3.8 ± 0.4 |
| NOD F | 1.0 ± 0.3 | 1.4 ± 0.5 | 2.4 ± 0.1* | 2.1 ± 1.2 | 1.2 ± 0.4 | 1.0 ± 0.6 | 1.5 ± 0.7 |
| NOD SCID F | 0.8 ± 0.4 | 0.8 ± 0.2 | 2.2 ± 1.3 | 1.0 ± 0.8 | 0.9 ± 0.2 | 0.5 ± 0.4 | 0.7 ± 0.2 |
| 4 wk Group | | | | | | | |
| BALB/c M | 1.0 ± 0 | 1.0 ± 0 | 1.0 ± 0 | 1.0 ± 0 | 1.0 ± 0 | 1.0 ± 0 | 1.0 ± 0 |
| NOD M | 1.0 ± 0.1 | 1.8 ± 0.8 | 5.2 ± 0.3*** | 0.6 ± 0.3 | 1.1 ± 0.5 | 1.2 ± 0.5 | 2.6 ± 1.4 |
| BALB/c F | 2.1 ± 1.5 | 0.9 ± 0.4 | 1.4 ± 0.5 | 1.0 ± 0.8 | 1.0 ± 0.2 | 1.6 ± 0.3* | 3.6 ± 1.1* |
| NOD F | 0.6 ± 0.3 | 0.5 ± 0.1 | 1.3 ± 0.4 | 0.5 ± 0.2 | 0.6 ± 0.2 | 1.0 ± 0.6 | 1.0 ± 0.2 |

***P value < 0.001;

**P value < 0.01;

*P value < 0.05.

ND, not detected. Each data point depicts the average of 3-5 PCR assays and errors are presented as ± standard deviation (SD). Each PCR assay was conducted on a different pooled RNA sample prepared from three to four mice.

5 male mice of each strain each aged 12 weeks were used for LG collection and isolation of interstitial inflammatory cells as previously described. B220+ CD19−, characterized as early B lymphoid progenitor cell; B220+ CD19+, B lymphoid progenitor cell; CD4+ CD8−, mature T helper cell; CD4− CD8+, mature cytotoxic T cell; CD11b+ GR1−, macrophage; CD11b+ GR1+, myeloid immunoregulatory cell; CD11b− GR1+, granulocytes; Pan-NK, NK cell. Percentage of each cell lineage was obtained by the cell number of a specific cell subset divided by total cell counts analyzed, then multiplied by 100%.

Female NOD and BALB/c mice, and 4-week-old NOD and BALB/c mice of both genders were also analyzed concomitantly. The results are summarized in FIG. 1. The expressions of the cytokines which were not detected by microarray, possibly due to low abundance, were also re-evaluated by this method. Consistent with the microarray analysis, the mRNA levels of Ctsh, Ctss and Ctsz in the 12 week old male NOD mouse LG were markedly higher than in the BALB/c mice as shown in FIG. 1A; all the macrophage-produced cytokines tested also showed markedly increased expression in the LG of NOD mice to different extents as shown in FIG. 1C. Interestingly, the mRNAs levels of the obesity-induced proteins Ctsh, Ctsz, Ctss, 11-6 and INF-$\alpha$ were all higher in NOD SCID mice than in BALB/c mice although the levels in NOD SCID mice were still lower than those detected in NOD mice (FIG. 1A); NOD SCID mice, like NOD mice, exhibit notable lipid deposition in the LG of the male mice. IL-10 was the only gene which exhibited equivalent elevated expression between male NOD and NOD SCID mouse LG (FIG. 1C). Comparison of gene expression levels in mice aged 4 weeks showed little to no changes in these same markers (FIGS. 1B and 1D). This age of 4 weeks is prior to the onset of lipid deposition and accumulation.

Macrophages are prominent infiltrating cells in diseased LG. A previous study has revealed the presence of various types of infiltrating immune cells including macrophages, neutrophilic and eosinophilic granulocytes, B-cells and T-cells within the LG of NOD mice at 18 weeks of age (Schenke-Layland et al., 2008). The expression profiles of cathepsins and cytokines by real-time RT-PCR measured here also suggested the activation of macrophages in NOD mouse LG. To understand the role macrophages play in this inflammatory autoimmune disorder in this disease model, lineage classification was performed by FACS analysis with prepared immune cell populations from pooled LGs from 12-week-old male NOD, NOD SCID and BALB/c mice. Proportions of B-cells (B220+CD19+), T-cells (CD4+ and CD8+), macrophages (CD11b+) and other immune cells out of the whole immune cell population counted in the LGs of three strains are listed in Table 3. The result showed that macrophages constitute a major population (25%), the second large population after the B cells in NOD mouse LG. NOD SCID mice lack T and B cells and have only partial competence in the function of myeloid cells. Consistent with this, there were significantly low numbers of B-cells (B220+ CD19+) and T-cells (CD4+ and CD8+) detected from NOD SCID mouse LG compared to that from NOD mice. The numbers of these cell types were even lower than that from BALB/c mouse LG; on the other hand, the macrophage population within the LG of NOD SCID mice was increased to 11% in contrast to 7% in the LG of BALB/c mice. This number was still lower than that in matched NOD mouse LG due to the lack of stimulation by and communication with lymphocytes. Table 4 shows the results of a confirmatory study.

Figure 2:
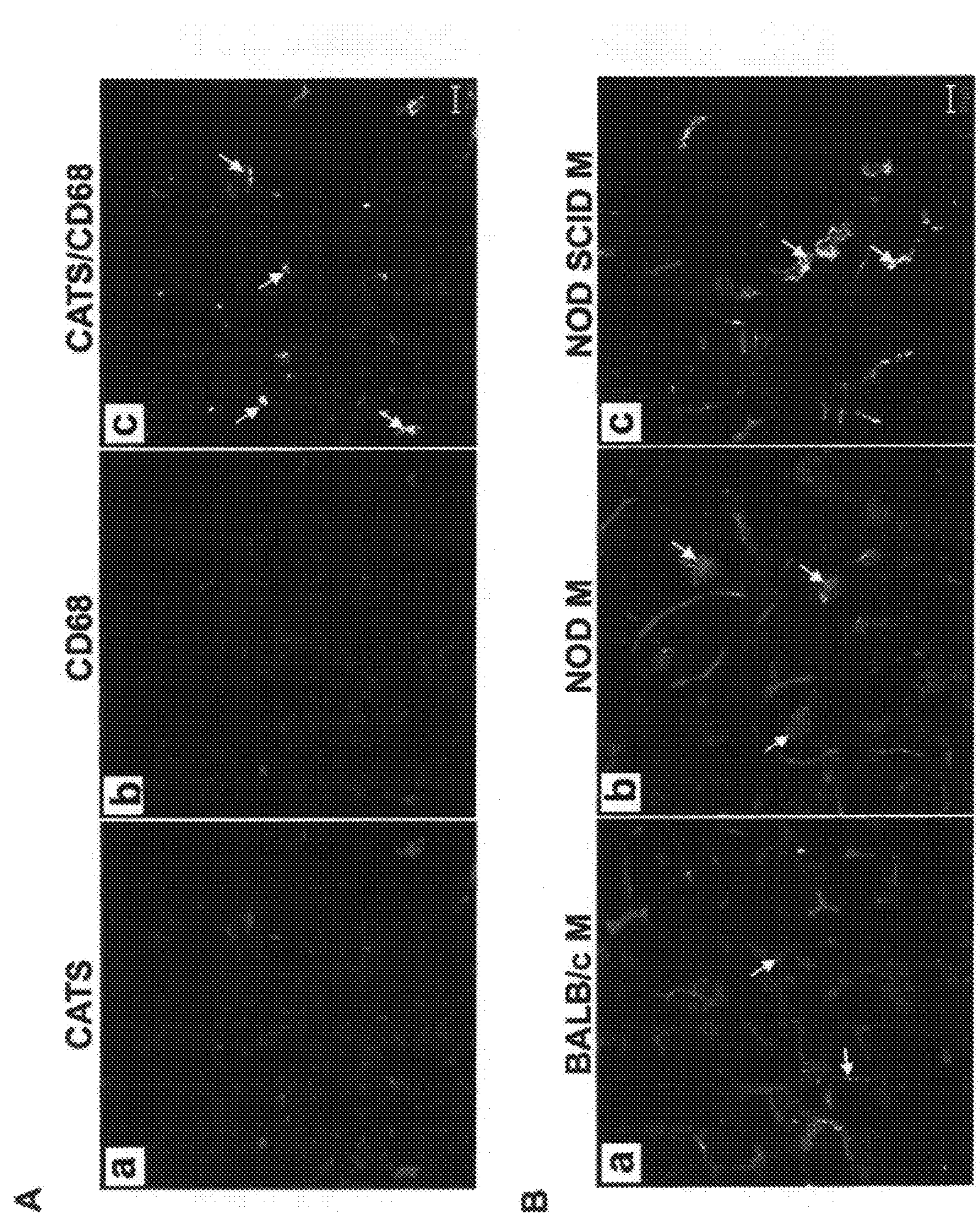
FIG. 2 shows the detection of CATS in different locations in LG from different mouse strains. Cryosections of LGs from 12-week-old male NOD, NOD SCID and BALB/c mice were incubated with goat anti-mouse CATS polyclonal antibody and rat anti-CD68 monoclonal antibody followed by appropriate fluorophore-conjugated secondary antibodies. The sections were imaged by confocal fluorescence microscopy. Nuclei were stained with DAPI (blue) and actin filaments with Alexa Fluor 647 (pink) in all panels to delineate the relative cellular location of the positive signals. Arrowheads point to CATS (red)-positive cells in the surrounding region of the LG; arrows to CATS-positive cells in the interior region of the LG; hollow arrowheads to CATS- and CD68 (green)-positive cells in the surrounding region of the glands; and arrows to CATS and CD68-double positive cells in the interior region of the gland. Bars=10 μm.

Characterization of CATS protein distribution in LG within macrophages and acinar cells. Previous studies demonstrated that CATS participates in both antigen presentation and normal cellular protein turnover and also degrades extracellular matrix in cancers. The extensive extracellular matrix degradation and immune cell infiltration combined with the gene expression profiling result from the current study indicated that the increased expression of CATS may directly contribute to LG destruction by degrading the extracellular matrix or alternatively that it may indirectly contribute to LG destruction by stimulating neoautoantigen presentation and consequent lymphocyte proliferation. Hence, the localization and abundance of CATS protein in LG was investigated using immunofluorescence microscopy. The results showed that CATS was present in populations of CD68-positive and -negative infiltrating cells (FIG. 2) within the LG. It was also noted that the distribution pattern of CATS was very similar to that of CATH. Both CATS-positive cells were within the connective tissues surrounding the LG of the all three strains, whereas CATS-enriched cells in the interior region of the gland were only detected in LG from NOD and NOD SCID mice. Additionally, CATS-positive cells were seen among the lymphocytic foci in the LG of NOD mice.

Figure 3:
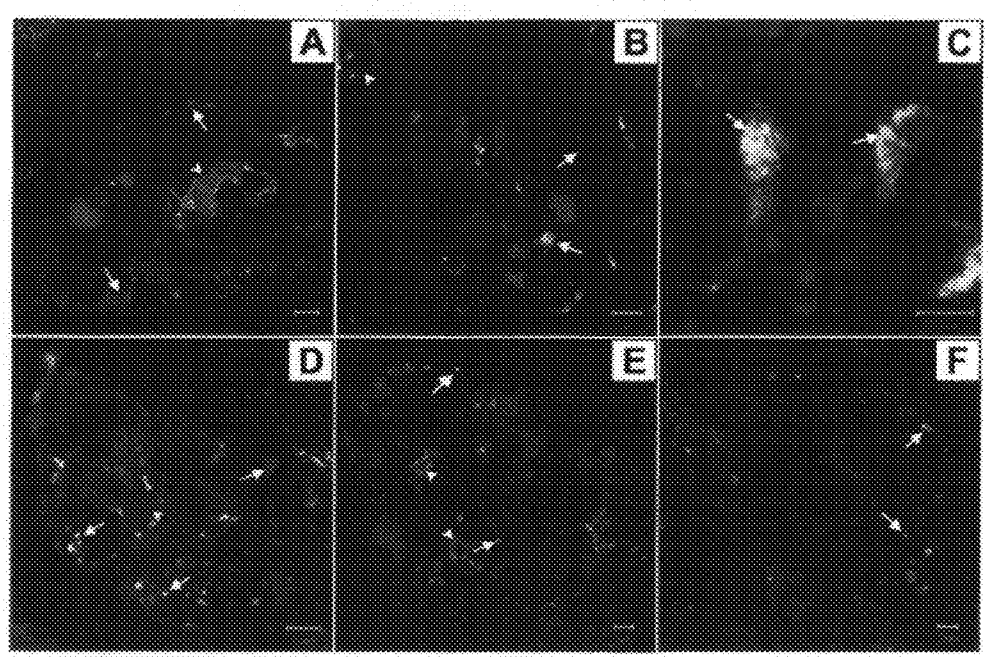
FIG. 3 illustrates the redistribution of CATS protein in LG acinar cells from NOD and NOD SCID mice. Cryosections of LGs from 12-week-old male NOD, NOD SCID and BALB/c mice were incubated with goat anti-mouse CATS polyclonal antibody and rat anti-Lamp2 monoclonal antibody followed by appropriate fluorophore-conjugated secondary antibodies. The sections were imaged by confocal fluorescence microscopy. Lamp2-enriched vesicles marked late endosomes/lysosomes. Labeling with DAPI (blue) for nuclei and Alex Fluor 647 (pink) for actin filaments was conducted to delineate the relative location of the targets; Arrowheads point to the CATS (red)-positive areas; arrows to the Lamp2-positive areas. Bars=10 μm.

CATS immunofluorescence was also detected within the acinar cells in addition to the macrophage and the other cell types described above. The number and size of Lamp2-positive late endosomes/lysosome and the abundance of the CATS protein appeared to be markedly increased in acinar cells from NOD (FIG. 3A) and NOD SCID (FIG. 3B) mice relative to the amounts in acinar cells from LG from matched BALB/c mice (FIG. 3C). CATS was also detected in the organelles in the subapical region surrounding the lumen of acinar cells from NOD (FIG. 3D) and NOD SCID (FIG. 3E) mice in contrast to the solely basolateral punctate labeling for CATS in the acinar cells from BALB/c mice (FIG. 3F).

Figure 4:
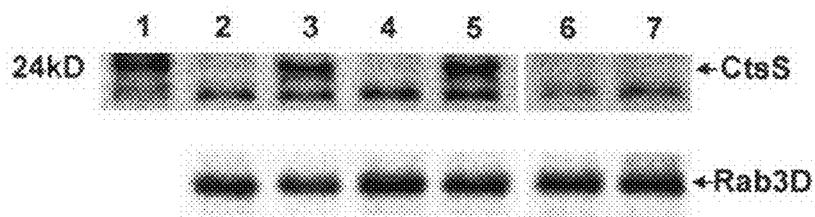
FIG. 4 shows comparison of CATS abundance and activity of LG between NOD and BALB/c mice. A: Western blotting to compare the protein abundance of CATS. LG lysates were prepared from 12-week-old male NOD mice or matched BALB/c mice. 100 μg each of LG lysates was loaded in each well of a 11% SDS-polyacrylamide gel. 50 μg of Raw264.7 cell lysate was run in parallel as a positive control. The proteins transferred to nitrocellular membrane were hybridized with goat anti-CATS polyclonal antibody. One of the two membranes prepared in parallel was hybridized with rabbit anti-Rab3D antibody as a loading control; this protein is highly abundant in LG. B: CATS activity assay. Left: 10 μg each of paired LG lysates from the two strains (n=X pairs) were incubated for 1, 2 and 18 hours and the fluorescence of the products was measured at excitation/emission wave lengths of 400/505 nm. The enzymatic activity is expressed as fluorescent units; error bars show SEM. Right: Assays were conducted as described with the addition of CATS inhibitor to the reactions to verify the specificity of the enzyme in the LG lysates.
Figure 4:
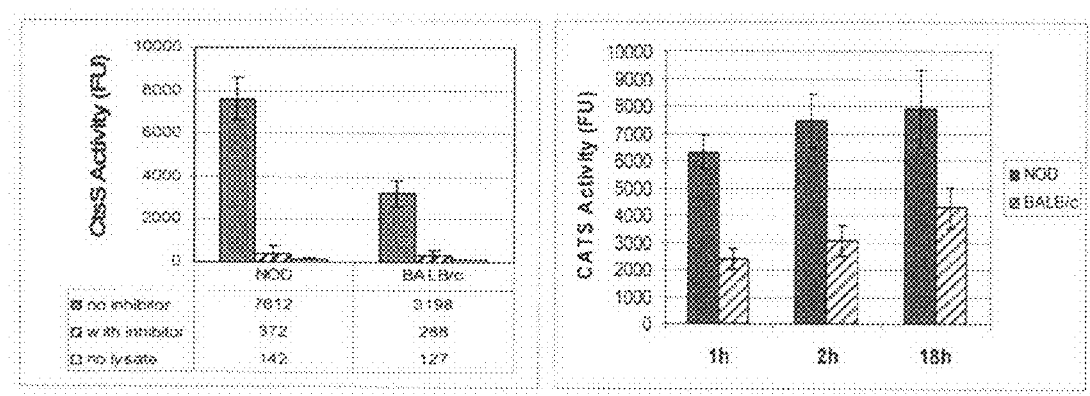

Increased abundance and activity of CATS in NOD mouse LG lysates and tears. The increased copy number of Ctss mRNA, the detection of additional CATS-positive cells in NOD mouse LG, and the detection of increased CATS immunofluorescence within subapical compartments in acinar cells described above all suggest an increased protein abundance and catalytic activity of CATS in LG under these pathological conditions. The CATS abundance was thus compared in LG of NOD mice to that of BALB/c mice by Western blotting analysis (FIG. 4A). Consistently, a clear 24 kD MW protein band corresponding to the molecular weight of active form of CATS in the gland lysate from NOD mice was detected (4A) but a much weaker to no band at the same position in LG lysate from BALB/c mice (4A). Enzymatic activity assays were also conducted for comparison of the CATS activities in LG between the two strains (FIG. 4B). The result showed the average CATS activity from NOD mouse LG lysates was significantly greater than that from the control BALB/c mice LG lysates.

Figure 5:
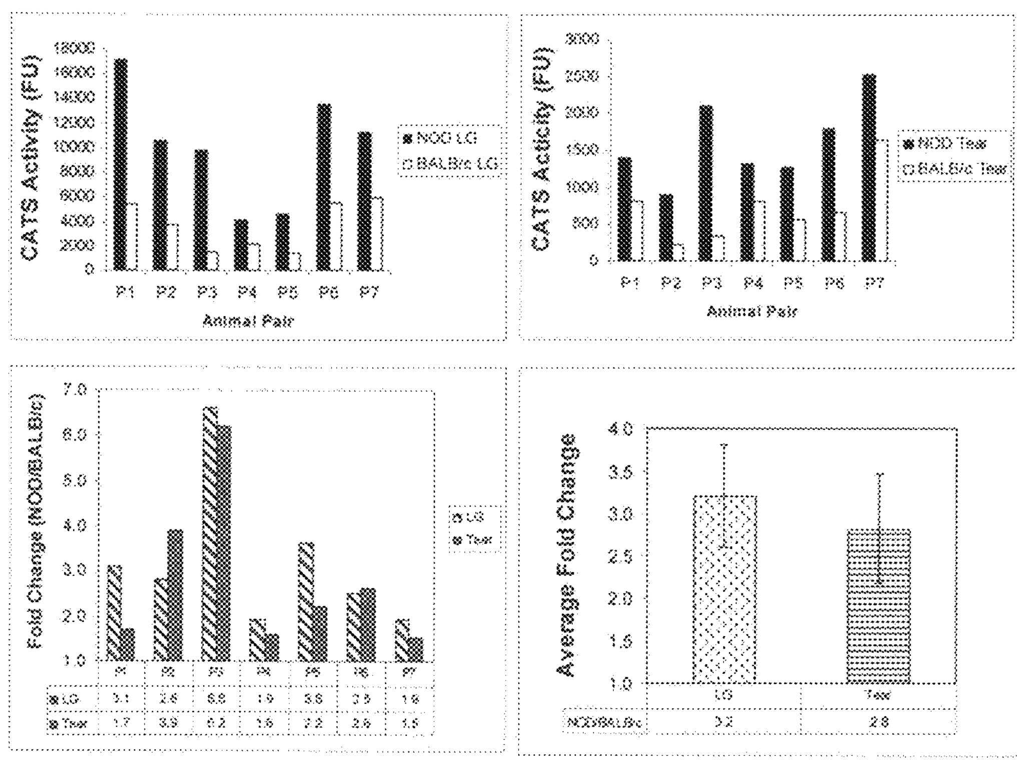
FIG. 5 shows comparison of CATS enzymatic activities from stimulated LG lysates and tear fluid between NOD and BALB/c mice. Mice were anesthetized and tear fluid collected following stimulation with CCH as described in Materials and Methods. Catalytic activity was assayed in the absence or presence of the specific CATS inhibitor used in FIG. 4. A: CATS activity in stimulated glands (n=X). B: CATS activity in collected tears from the stimulated glands (n=Y). C: CATD activities in stimulated LG and tears between the paired NOD and BALB/c mice (n=Z).
Figure 5:
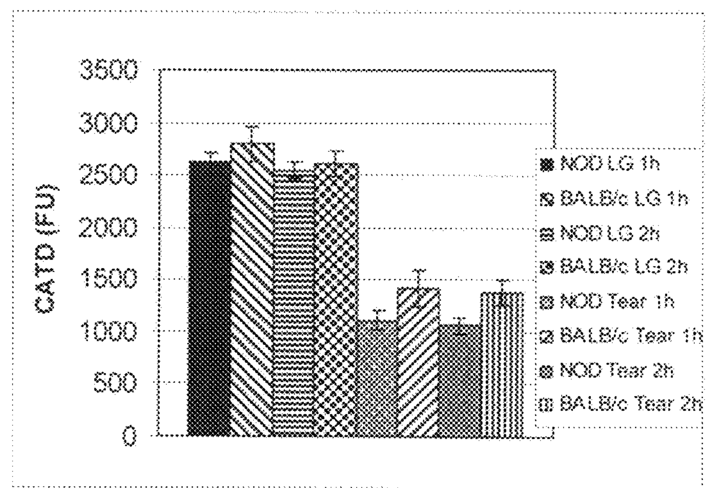

The evident redistribution of CATS immunofluorescence into apparent subapical secretory vesicle-like organelles as well as within the lumena in the acinar cells suggested that CATS may be actively secreted at the apical membrane into the tear fluid in NOD mice. Hence the enzymatic activities of the tears were measured in the absence or presence of specific inhibitor, in parallel with the LG lysate. The results demonstrated significantly higher CATS activities in tear fluid of NOD mice relative to those of BALB/c mice upon stimulation of the LG with the agonist, CCH (FIG. 5). Consistent with the testing results from LG lysates, the average enzymatic activity of the tears collected was measured from the stimulated glands of NOD mice versus from that of BALB/c mice.

Cathepsin D, like CATH and CATS, is another member of peptidase Cl family expressed in LG (Table 1). Using this activity as a control activity with expression unchanged in the NOD strain relative to the BALB/c strain, no differences in either catalytic activities or gland lysates or tears was detected between the two mouse strains, consistent with the result of the microarray (FIG. 5C).

Figure 6:
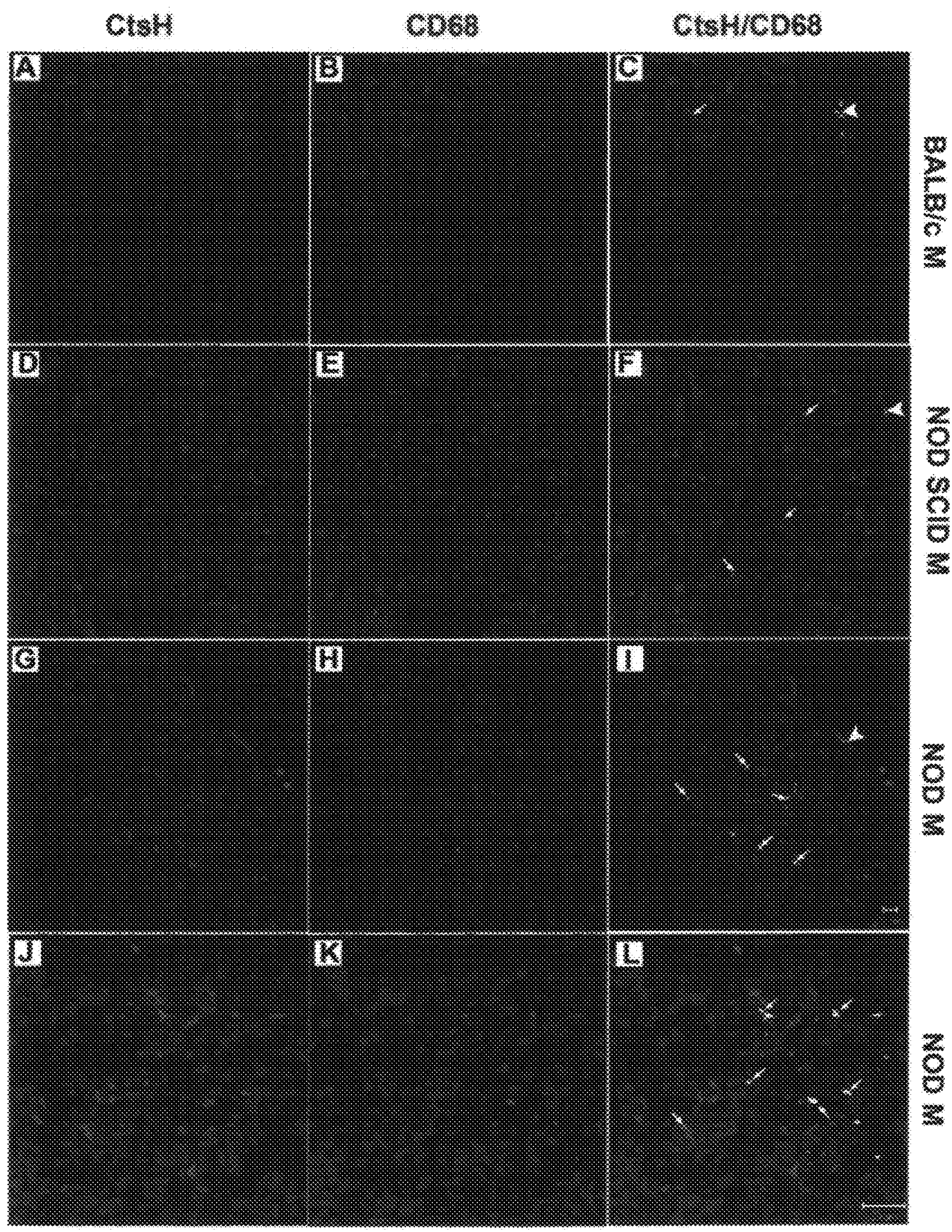
FIG. 6 shows detection of CATH in different locations in LG from different mouse strains. Cryosections of LGs from 12-week-old male NOD, NOD SCID and BALB/c mice were incubated with goat anti-mouse CATH polyclonal antibody and rat anti-CD68 monoclonal antibody followed by fluorophore-conjugated secondary antibodies. The sections were imaged by confocal fluorescence microscopy. CD68-positive cells are macrophages. DAPI (blue) for nuclei and Alex Fluor 647 (pink) for actin filaments were used to delineate the relative location of the targets. Arrowheads point to CATH (red)-positive cells in the surrounding region of the LG; arrows to CATH-positive cells in the interior region of the LG; Hollow arrowheads to CATH- and CD68 (green)-positive cells in the surrounding region of the glands; and arrows to CATH- and CD68-double positive cells in the interior region of the glands. Bars=10 μm.

Characterization of CATH protein within macrophages but not acinar cells in LG. CATH is defined as an aminopeptidase (notably, cleaving Arg-|-Xaa bonds) as well as an endopeptidase. Its cellular function is somewhat obscure to date. Its mRNA was markedly elevated in the NOD mouse LG. Immunofluorescent microscopy was performed to localize the cells producing CATH protein. The results are shown in FIG. 6. Similar to the distribution of CATS, the CATH protein was observed in some cells in interstitial and elastic tissue within the sac surrounding the LG in NOD, NOD SCID and BALB/c mice (FIGS. 6B, F and J). The CATH-positive cells were also enriched at the intercellular space between the acini from NOD and NOD SCID mice but not from BALB/c mice (FIGS. 6F and J). In addition, CATH-positive cells were observed among the infiltrating foci in the LG of NOD mice (N). Some but not all CATH-positive cells were also positive for CD68 and these cells were seen either at the extracellular space or within the foci (FIGS. 6C, D, G, H, K, L, O and P). Unlike CATS, no CATH protein was detected in the acinar cell.

Figure 7:
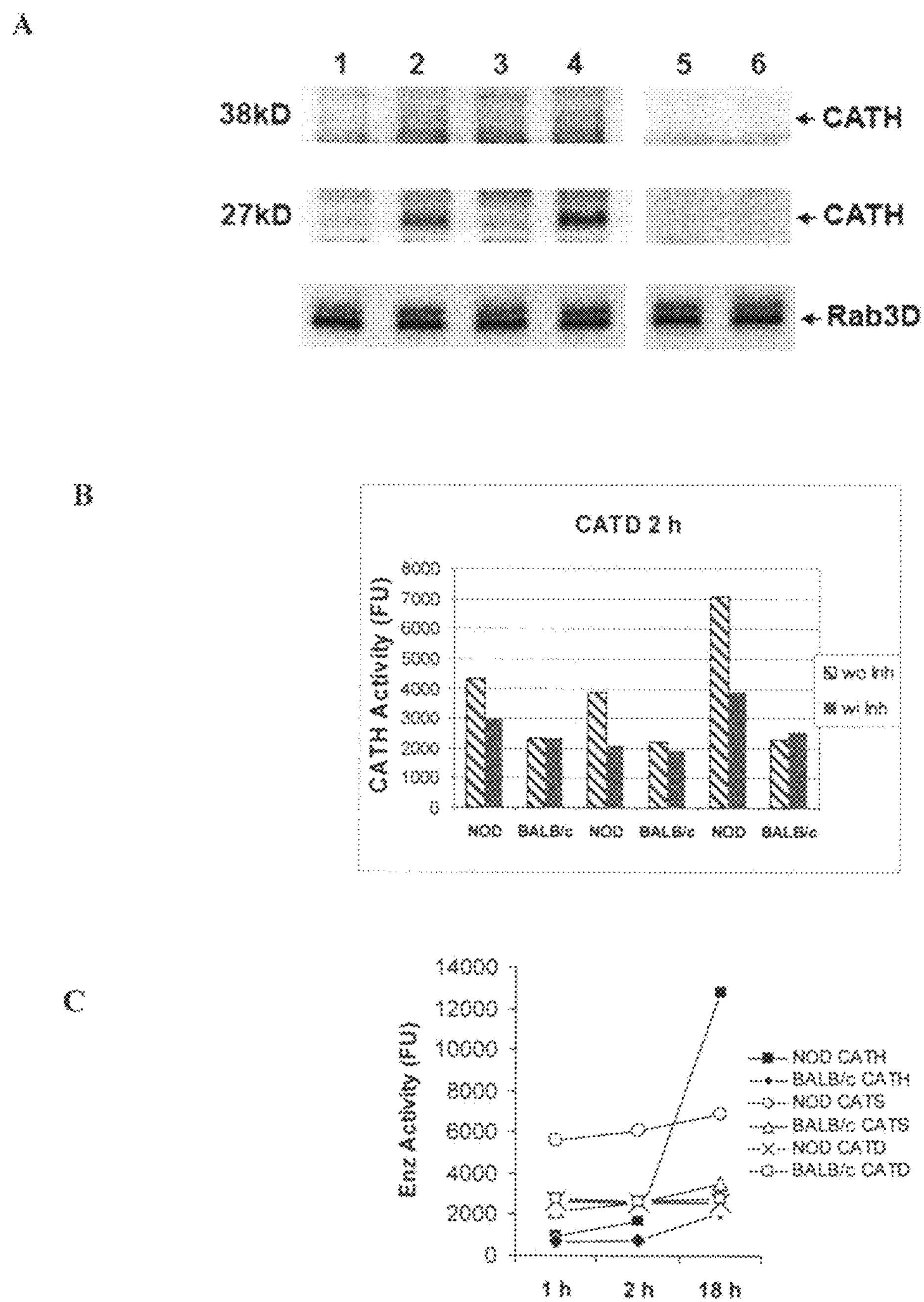
FIG. 7 illustrates the comparison of CATH abundance and activity in LG lysates from NOD and BALB/c mice. A: Western blotting to compare the protein abundance. LG tissue lysates was prepared from 12-week-old male NOD mice or matched BALB/c mice. 100 μg each of LG lysates was loaded to each well of 11% SDS-polyacrylamide gel. 50 μg of Raw264.7 cell lysate was run in parallel as positive control. The proteins transferred to nitrocellular membrane were hybridized with rat anti-CATH monoclonal antibody. One of the two membranes prepared in parallel was hybridized with rabbit anti-Rab3D polyclonal antibody as the loading control. B and C: CATH activity assay. C: 10 μg each of paired LG lysates from the two strains (n=3 pairs) were analyzed for 1, 2 and 18 hours and the fluorescence of the products was measured at excitation/emission wave lengths of 400/505 nm. The enzymatic activity was presented as fluorescent units; error bars depict SEM. B: CATH inhibitor was added to the reactions to verify the specificity of the enzyme in the LG lysates.

Western blotting analysis was conducted to investigate if the abundance of CATH protein also increased in parallel with the elevated mRNA levels in NOD mouse LG. The result showed that there were two protein bands recognized by the anti-CATH antibody with approximate molecular weights of 37 and 27 kD, corresponding to the full length protein and the active cleaved form of CATH, respectively (FIG. 7A). The abundance of CATH, especially the active form, was significantly higher in the lysates of LGs from NOD mice than from BALB/c mice.

The enzymatic activity of CATH was also determined as shown in FIGS. 7B and 7C. Significantly elevated catalytic activity of the enzyme was detected in LG lysates from 12-week-old male NOD mice versus that from the matched BALB/c mice. We noted that CATH remained catalytically active for an extended period of time, especially in the assay with NOD mouse LG lysates, in comparison to CATS and CATD. Additionally, the catalyzing activity was only partially inhibited by the CATH inhibitor (FIG. 7C), indicating a likely contribution of the partial activity by other non-CATH enzyme(s) or limited inhibitory ability of the inhibitor (FIG. 7B).

Discussion

The experiment described above reports, for the first time, the significant upregulation of CATS expression and activity in the LG during development of autoimmune inflammatory disease. Applicants' data further suggests, as specified below, that CATS expression is upregulated in both the infiltrating immune cells as well as in the acinar cells that constitute the bulk of the gland, suggesting a complex role for CATS in etiology of disease Consistent with gene expression analysis, CATS-positive cells are detected more abundantly in the NOD mouse LG than in the BALB/c mouse LG. CATS protein was detected in a vast number of the infiltrating cells in the NOD mouse LG within foci as well as at the LG periphery, but was only detected in some macrophage-like cells in the peripheral connective tissue-enriched areas of the BALB/c mouse LG. While many of the CATS-enriched cells within inflammatory cell foci in the NOD mouse LG were CATS+/CD68+, confirming their identity as macrophages, a considerable number of CATS-positive cells were CD68-negative, suggesting the presence of other antigen presenting cells (APC). Additionally, a notable proportion of CATS positive cells were extremely lysosome rich as evidenced by their enrichment in Lamp2 staining. These observations are consistent with previously established mechanisms for the role of CATS in antigen presentation and cellular protein maturation in macrophages and other APCs, which contribute to activation of T-, B- and other lymphocytes.

Beside the CATS-positive immune cells, CATS immunofluorescence and, by extension, protein abundance was also significantly increased in the acinar cells from NOD and NOD SCID mouse LG versus that from BALB/c mice. The acinar cells constitute approximately 85% of the cell mass of the LG and are largely responsible for production and release of secretory proteins into the tears. They therefore maintain an abundant array of mature secretory vesicles within their subapical cytoplasm. A subset of CATS-enriched organelles within the acinar cells was significantly co-localized with markers within the acini. These findings suggested stimulated biogenesis of lysosomal-like organelles in acini from NOD mouse LG. A subset of CATS was also detected within very large secretory vesicle-like organdies localized in the sub-apical region, as well as within the lumena of the acini of NOD and NOD SCID mice, but not in the acini of BALB/c mice, indicating altered protein sorting and apical secretion for CATS in the NOD background. This finding was verified, in the NOD mouse, by the detection of increased CATS activity in tears relative to the BALB/c control strain. Routinely, newly synthesized lysosomal proteins such as CATS are processed in the endoplasmic reticulum (ER) and Golgi apparatus to the trans-Golgi network (TGN), then are actively sorted to lysosomes via late endosomes as the terminal destination. This sorting path appears to be partially altered in NOD mouse with a diversion of some of the upregulated CATS into the regulated apical secretory pathway. This missorting may arise from one of two possibilities: 1) CATS overproduction may saturate the normal sorting pathways in the TGN such as mannose-6-phosphate receptors and others that sequester lysosomal proteins into cargo vesicles destined for lysosomes, and thus the extra CATS may traffic through a default pathway into mature secretory vesicles; 2) CATS may be actively missorted into this path due to a fundamental abnormality in the cellular trafficking system of NOD (and NOD-SCID) mice.

While CATD is known to be an established lysosomal resident protein, it is also known to be a component of normal tear fluid, consistent with our unpublished proteomic data in the mouse. Gene expression microarray showed no change in CATD expression at the mRNA level, and the corresponding enzymatic analyses showed no changes in either LG tissue or tears from NOD mice compared to the control, despite the significant elevation of CATS activity. Therefore it appears that CATD is not involved in nor influenced by the disease progression in NOD mouse LG. This result is supportive of option 1, i.e., that the intracellular sorting of lysosomal proteins is regulated by the abundance of each respective protein, since only the upregulated CATS and not the normally-expressed CATD are missorted to secretory vesicles. However, membrane trafficking is highly dependent on lipid membrane composition, and lipid-enriched subdomains or "lipid rafts" are known to serve as signaling platforms and to mediate specific internalization events such as caveolar endocytosis, so option 2 is consistent with the lipid metabolic abnormalities in the acinar cells from NOD mice, particularly if different sorting processes are involved in capture of CATD and CATS to lysosomes. Regardless of cause, this collective observations of increased lysosomal abundance in parallel with missorting of lysosomal proteins into the regulated secretory pathway effect demonstrates global changes in protein sorting and processing within the acinar cells that may contribute significantly to pathology. The increased CATS and lysosomal activity suggests enhanced and possibly abnormal protein degradation and processing which may enhance CATS production of neoautoantigens in the altered lysosomal pathway of the acinar cells, while enhanced CATS activity in tears may result in tear protein degradation and also extracellular matrix damage to the ocular surface.

In addition to CATS, the spectrum of upregulated inflammatory cytokines that accompany CATS upregulation in obesity were also detected in the NOD mouse LG. Applicants hypothesize that these cytokines are largely produced by infiltrating macrophages, based on the following reasoning. The LG of NOD SCID mice still retains macrophages at an increased number relative to BALB/c mice although not as many as in the NOD mice, while it lacks T and B lymphocytes. In parallel, increased mRNAs of Tnfa, I16 and I110 were detected in NOD SCID mouse LG relative to BALB/c mice although to a less extent compared with NOD mice. These results suggest that the macrophages present in the LG of NOD mice, compared to NOD SCID mice, are further stimulated by lymphocytes resulting in the increase in their number in parallel with the more vigorous inflammatory response.

CATH protein, also significantly upregulated in NOD mouse LG relative to BALB/C mouse LG, was exclusively detected in non-acinar cells including cells migrating into the extracellular space between acini as well within infiltrating foci. Applicants also noted a corresponding increase in CATH enzymatic activity within NOD LG lysates. Persistent conversion of the substrates into products in the proteolytic activity assay during an 18 hr extended time course indicates that CATH has a stable and long lasting activity in vivo compared to CATS. Partial co-localization of CATH immunofluoresence with that of CD68 indicates some of CATH-positive cells are macrophages. The physical locations of CATH suggest its involvement in macrophages and other inflammatory cell functions. Previous studies reported that this enzyme is secreted from neutrophils and participates in the degradation of extracellular matrix. The extensive loss of extracellular matrix within the NOD mouse LG that has previously been reported thus renders CATH a candidate for this pathological event in the NOD mouse model.

The increased protease activity of CATS and CATH within the LG has multiple possible consequences. First, the increase in CATS-enriched lysosomes labeled with Lamp2 suggests that lysosomal degradative capacity may be enhanced, thus raising the possibility that protease degradation of proteins in lysosomes becames abnormal. Previous work has suggested that alterations in proteolytic activity may expose cryptic epitopes on otherwise tolerated self-proteins, which may be effluxed or recycled into the interstitium from the late endosomal compartments where they may encounter increased CATS. Cryptic epitopes in the interstitium may encounter primed APC and macrophages, thus potentiating autoimmunity. Likewise, CATS activity on the ocular surface and CATH activity within the tissue may promote loss of extracellular matrix in the ocular surface system.

The detection of proteolytic activity of CATS in the tear fluid of NOD mouse in parallel with the detection of CATS immunoreactivity in subapical secretory vesicles shows that this enzyme is secreted from acinar cells. This fact suggests the possibility that the CATS in tears may digest certain protein components of the cornea, therefore damage the integrity of the ocular surface as well as enhancing sensory input from the cornea to the LG, an event that has been previously linked to the functional quiescence that characterizes the LG in SjS. Since cathepsins have collagenase/elastinase activity, the presence of both CATS and CATH in macrophages and other interstitial cells may also degrade tissue extracellular matrix, thus expediting the infiltration of immune cells and the loss of secreting function. Targeting CATS and CATH may therefore constitute alternative therapeutic strategies in the treatment of chronic autoimmune dacryoadenitis associated with SjS.

In summary, the NOD mouse model is an established model of SjS-like chronic autoimmune dacryoadenitis. Specific cathepsin family members and cytokines are upregulated during development and progression of disease in this mouse model, with a profile comparable to those changes seen in obesity, suggesting that the lipid deposition plays a causal role in the autoimmune inflammatory response. The profile of increased cathepsin protease expression and distribution within macrophages, other APCs and even within acinar cells suggest a complex role for these proteases in initiation and progression of autoimmunity. Overexpressed CATS secreted into the tear fluid from NOD mice reflects the initiation of disease and the consequent changes in LG function and thus may serve as a biomarker for diagnosis of autoimmune dacryoadenitis in human. CATS and CATH may also be considered as potential targets for alternative therapeutic approaches to treat and prevent progression of SjS, particularly if ways can be identified to specifically target such inhibitors to the sites of interest within the LG.

Experiment 2

SjS Biomarkers in Tears are Correlated with the Severity of Inflammatory Autoimmune Lacrimal Gland Disease.

Applicants can utilize three unique tear biomarkers for SjS, CtsS, Apo-F and Lcn-2, that will be expressed in tears at levels proportional to the extent of inflammatory autoimmune LG disease manifested in the source of the tears. In mouse and human tears, levels of these three biomarkers are quantified, and submitted to be increased in disease, in parallel with three tear secretory proteins, lactoferrin, lactoperoxidase and lysozyme, submitted to be generally decreased in SjS as well as other KCS disorders. Therapeutic efficacy of the claimed methods can be monitored by monitoring the expression of these biomarkers.

The NOD mouse and the IL1-injected BALB/c mouse represent two models of inflammatory autoimmune LG disease. Tears and ocular tissue samples are collected from these models at intervals relevant to disease development and progression. In parallel, the extent of inflammatory autoimmune LG disease is quantified by analysis of cornea, conjunctiva and LG. All biomarkers will additionally be screened in tears from populations of control and primary SjS patients with established clinical symptoms. Analysis of biomarkers in tears will use standard Western blotting, ELISA or biochemical tests.

SjS patients. Patients with diagnosed primary SjS, according to the revised version of the European criteria proposed by the American-European Consensus Group, will be recruited from the Rubenstein Clinic at Tufts University and/or through the Doheny USC Corneal Clinic or County USC hospital. Age and sex-matched individuals with no history of autoimmune disease or KCS will be recruited. Tears will be collected by our collaborating Physicians, Michael Goldstein, John Irvine, Martin Heur, and William Stohl. Since the majority of SjS patients do not produce sufficient tears, these will be collected after an "eye-wash". Before tear collection, SjS patients (and controls) will undergo a thorough eye exam including Schirmer's test and vital staining of the ocular surface. This information can be used for correlation studies. Briefly, a drop of local anesthetic (to collect unstimulated or basal tears) will be first applied to the ocular surface followed by 2 drops of saline (because most SjS patients have no visible tears). To be consistent, tears will be collected from control subjects following the same protocol. The subjects will be asked to blink twice after which the fluid in the eye will be collected using a microcapillary tube under a slit lamp. Tears will be transferred to a microfuge tube, spun for 10 min at 12,000 rpm (4° C.) to remove potential cell debris, and then frozen at −80° C. until analysis. This method of collection yields a total volume of 8-14 μL/eye. This technique has previously been used to collect tears of adequate quality. Ongoing clinical investigations have also shown that these biomarkers can be collected and eluted from standard Schirmer's strips which are routinely used to diagnose dry eye disorders, and protocols which would replace the use of the microcapillary tube and use instead the Schirmer's strip material that would be already collected as part of the patient work up are in process. Such a modification of the collection protocol will greatly aid in ease of biomarker diagnosis for practicing physicians since it necessitates the use of material from a commonly applied clinical test rather than a new procedure.

Potential SjS biomarkers to be analyzed in tear fluid—predicted increase associated with disease. CtsS is a type of cathepsin, a major class of lysosomal proteases. They are established effectors of protein degradation within the lysosomes, and their activity is critical to additional activities including precursor protein activation, MHC II-mediated antigen presentation, reproduction and apoptosis (Turk et al. (2001) EMBO J. 20(17):4629-33). Several cathepsins are expressed in LG, but CtsS in particular has a compelling history related to autoimmunity. CtsS is highly expressed in antigen-presenting cells and is implicated in MHC II-mediated antigen presentation. It is implicated in the pathogenesis of degenerative immune diseases including chronic inflammation and rheumatoid arthritis. CtsS is also upregulated in response to lipid deposition, a feature of LG pathology strongly associated with inflammatory autoimmune disease in the NOD mouse LG. CtsS activity has been targeted therapeutically in a mouse model of SjS; SG and LG lymphocytic infiltration was prevented by prior administration of a CtsS inhibitor to SG. Significantly increased activity of CtsS in LG sections and tears from diseased male NOD mice is demonstrated. CtsS also shows an 11-fold increase in gene expression in male NOD mouse LG, relative to age-matched BALB/c mouse LG. The biochemical spectrophotometric assay illustrated in FIG. 9B will be utilized for measurements of CtsS activity in tears.

Apo-F is a constituent of HDL and LDL, and can be associated with cholesterol and cholesterol esters in lipoproteins. Very little is known about its biological function. Recent findings in the LG suggest that it may normally modulate cholesterol influx and/or excretion in LG at the basolateral membrane, and that its extensive upregulation, possibly in response to metabolic abnormalities and/or inflammation in diseased LGAC, may lead to its mis-sorting and apical excretion into tears (Wu, et al. (2009) Exp Eye Res.). Apo-F shows an 53-fold increase in gene expression in male NOD mouse LG, relative to age-matched BALB/c mouse LG, and its content in male NOD mouse tears is markedly increased relative to virtually undetectable levels in tears from age-matched BALB/c controls (Wu et al. (2009) Exp Eye Res.). Its presence and abundance in tears will be quantified by Western blotting in these proposed studies. To supplement mouse-specific Apo-F antibody, which will be used to probe mouse tears in healthy and diseased mice, Applicants have recently obtained a human-specific Apo-F antibody from Drs. Bill Lagor and Daniel Rador (University of Pennsylvania) that will be appropriate for immunoblotting of human tears from healthy and primary SjS patients.

Lcn-2, also called neutrophil gelatinase-associated lipocalin, is expressed in both mice and humans, and has been shown to be highly expressed in pancreatic islets, bone marrow, and SG. Until now its expression in LG has not been investigated but microarray data suggest moderate to high levels of expression. It is implicated in diverse bioprocesses including iron-siderophore binding in bacterial infections as a component of the innate immune system, modulation of inflammation, and is a marker closely related to obesity and insulin resistance (Flo et al. (2004) Nature 432(7019):917-21, 13). The upregulation of Lcn-2 in diseased NOD mouse LG relative to BALB/c mouse LG, suggests its utility as a putative tear biomarker. Like CtsS, its upregulation in diseased NOD mouse LG may be related to tissue lipid deposition which characterizes this animal model as well as SjS patients. Lcn-2 has also been reported to be upregulated under conditions of inflammation and by IL-1β and IFNγ cytokines.

Potential SjS biomarkers to be analyzed in tear fluid-predicted decrease associated with disease Lactoperoxidase, Lactoperoxidase is a secreted glycoprotein member of the peroxidase family. It has antimicrobial properties due to its ability to sequester calcium, iron and heme B, and also supplies a potent antioxidant activity to the tears through its ability to form reactive bromine and iodine species through hydrogen peroxide oxidation of halides (Ghibaudi & E. Laurenti (2003) Eur. J. Biochem. 270(22):4403-12). Its activity can be measured through simple spectrophotometric assays.

Lactoferrin, is also a secretory glycoprotein that is a member of the transferrin family. It is the principal iron-binding protein in milk and bodily secretions, providing a potent antimicrobial activity as part of the non-specific immune system. It has a broad range of activity including regulation of iron homeostasis, host defense, regulation of growth and differentiation and protection against cell transformation (Weinberg (2007) Curr. Pharm. Des. 13(8):801-11; Zimecki et al. (2007) J. Exp Ther. Oncol. 6(2):89-106). It can be assayed by ELISA using commercially available antibodies, or immuno-immobilization followed by enzymatic activity assays using commercially-available kits. Applicants have shown that it can be easily detected by Western blotting in tears from both healthy and SjS patients.

Lysozyme, is a secretory protein that is ubiquitously present in human serum, urine, tears and milk (Zimecki et al. (2007) J. Exp. Ther. Oncol. 6(2):89-106). It hydrolyzes glycosyl linkages present in the mucopolysaccharide cell wall of diverse organisms. It can be assayed using a simple fluorescence-based enzymatic activity assay that is commercially available.

Collection and analysis of tissues and fluids: In mouse models, a comprehensive series of established assays can be conducted to quantify the extent of disease development and progression including an analysis of tear flow and corneal integrity in the live animal, as well as the isolation and analysis of tissue integrity and inflammation in LG, cornea and conjunctiva after tear collection and sacrifice of the animal.

Tear flow and corneal integrity in live mice: For measurement of tear production and corneal integrity in live mice, cotton threads pre-impregnated with phenol red that turn red upon contact with tear fluid can be used. Mice can be anesthetized with 2-3% isoflurane. The thread is inserted into the lateral canthus for 30 sec with care not to touch the cornea. Wetting of the thread is evaluated under the magnifier by at least 2 evaluators and averaged in millimeters. After the measurement with the cotton thread or in separate populations of anesthetized mice, corneas are evaluated for any pathological signs as reflected by fluorescein staining in a dark room. One μL of freshly made 1% sodium fluorescein can be carefully applied to the lateral canthus and the eyelids manually blinked 3× to spread the solution. Excess solution can be removed by gently applying a Kimwipe tissue to the lateral canthus and corneal fluorescein staining is immediately (within 30 sec of addition) evaluated and photographed with a Motic microscope equipped with a CCD camera using a cobalt blue light. Images are evaluated and graded by a standard protocol. These tests are conducted on the same mice that can be subsequently be used for collection of tear fluid, LG and ocular surface tissue below, as long as the mice are allowed to recover from anesthesia for several hrs following the isoflurane.

Analysis of biomarker content of tear fluid: For collection of lacrimal fluid, mice can be anesthetized with ketamine/xylazine, placed on a heated surgical table and immobilized with non-penetrating steel pins. One LG can be exposed. The duct and gland can be freed via blunt dissection and care will be taken not to injure nearby nerves and blood vessels. The thin connective tissue capsule enclosing the gland can be carefully opened and removed. To limit the spread of the superfusate, the LG are covered with a Kimwipe mesh. Fluid is drained from the mesh with a rigid aspiration pipette. Drugs and chemicals can be added to the superfusate with a wash-in time of ~30 seconds. A microcapillary tube can be placed near the lacrimal duct to collect basal and stimulated tear fluid. After fluid from one gland has been collected the other gland will be similarly exposed for collection of tear fluid.

A mouse typically yields about 1 μL of tear fluid, varying according to the age, gender and extent of disease development. All biomarkers in pooled mouse tear samples, from 5 mice per experimental data point, can be analyzed. A least 5 separate assays points can be obtained from pooled specimens under each disease condition or time point. Assays can vary according to the biomarker under study. For CtsS, lactoperoxidase, and lysozyme enzymatic activity can be measured while for Apo-F, Lcn-2 and lactoferrin either Western blotting or ELISA can be used. For Lcn-2 measurement the cyclotide-based assay described in previous paragraphs can be used.

Analysis of ocular surface and LG disease: At the conclusion of the tear collection, eyeballs from experimental animals and LG can be isolated and either flash frozen or paraffin-embedded according to standard methods to obtain tissue sections for immunofluorescence microscopy or histology. Sections from LG can be stained with hematoxylin and eosin to evaluate cytoarchitecture and to assess lymphocytic infiltration. If evidence for lymphocytic infiltration is seen, extent of lymphocytic infiltration will be quantified per unit area of LG and the identify of infiltrating cells (T cells, B cells, macrophages) may be further assessed using indirect immunofluorescence of frozen sections and appropriate commercial primary and secondary antibodies. Whole LG and measure levels of inflammatory cytokines using RT-PCR as evidence of inflammatory disease. Corneal and conjunctival sections from control and disease model mice can be processed with Movat's pentachrome stain or Periodic-Schiff's reagent to detect loss of goblet cells and mucins and corneal stromal damage, both of which are established as markers for ocular surface damage (Dursun et al. (2002) Adv. Exp. Med. Biol. 506(Pt A):647-55). The same sections can be analyzed by hematoxylin and eosin staining to evaluate possible lymphocytic infiltration, and if seen, the composition of the infiltrates can be analyzed by indirect immunofluorescence as above.

Measurement of biomarkers in tears and LG: Activity (CtsS, Lactoperoxidase, Lysozyme) or protein content (Apo-F, lactoferrin, Lcn-2) can be measured as described for each protein in the preceding biomarkers section, and signal normalized both to tear volume collected as well as total tear protein. This latter calculation can be particularly important since in some of the primary SjS patients, tears may need to be collected by gentle washing of the ocular surface because of the complete loss of fluid flow. To understand how changes in tear composition may be due to disease-specific changes in gene expression of the proteins, Applicants can conduct real-time PCR analysis of the relative mRNA content for each protein. This can help in determining the most specific biomarkers that are most directly associated with severe inflammatory disease.

Interpretation and Challenges: Applicants predict that the abundance of each of the disease-induced biomarkers (CtsS, Apo-F and Lcn-2) in tears from control animals will be minimal, and that their content in the tears will increase in proportion to the severity of autoimmune inflammatory disease in the mouse models. It has never been explored whether the expression of these biomarkers increases as disease progresses in the NOD mouse, beyond the 4-12 week time-points measured so far at disease onset. It has also never been explored whether these biomarkers are secreted into tears in any other mouse model of disease. These potential novel biomarkers are newly discovered and have also never been comparatively measured in healthy and primary SjS patient tears. The parallel measurement of gene expression using real-time PCR can aid Applicants in identifying markers that are uniquely upregulated and secreted to tears in inflammatory autoimmune disease. Such an increase over a low background or threshold would be ideal for translational development as a biomarker of disease.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A method of treating a mammal suffering from primary or secondary Sjögren's Syndrome (SjS) consisting essentially of administering to the mammal an effective amount of rapamycin.

2. The method of claim 1, wherein the mammal is a murine, a simian, a leporid, or a human patient.

3. The method of claim 1, wherein the treatment comprises reducing the symptoms of dry eye and/or tear loss.

4. The method of claim 1, wherein rapamycin is administered locally or systemically.

* * * * *

SEQUENCE LISTING

```
<160> NUMBER OF SEQ ID NOS: 8

<210> SEQ ID NO 1
<211> LENGTH: 10
<212> TYPE: PRT
<213> ORGANISM: Human herpesvirus 8

<400> SEQUENCE: 1

Glu Val Val Leu Phe Leu Leu Asn Val Phe
1               5                   10


<210> SEQ ID NO 2
<211> LENGTH: 12
<212> TYPE: PRT
<213> ORGANISM: Human herpesvirus 8

<400> SEQUENCE: 2

Gln Thr Phe Leu His Trp Val Tyr Cys Met Glu Asn
1               5                   10


<210> SEQ ID NO 3
<211> LENGTH: 10
<212> TYPE: PRT
<213> ORGANISM: Unknown
<220> FEATURE:
<223> OTHER INFORMATION: Description of Unknown: Viral FLICE-like
      inhibitor protein

<400> SEQUENCE: 3

Glu Met Leu Leu Phe Leu Cys Arg Asp Val
1               5                   10


<210> SEQ ID NO 4
<211> LENGTH: 12
<212> TYPE: PRT
<213> ORGANISM: Unknown
<220> FEATURE:
<223> OTHER INFORMATION: Description of Unknown: Cellular FLICE-like
      inhibitor protein

<400> SEQUENCE: 4

Lys Ser Phe Leu Asp Leu Val Val Glu Leu Glu Lys
1               5                   10


<210> SEQ ID NO 5
<211> LENGTH: 10
<212> TYPE: PRT
<213> ORGANISM: Herpesvirus saimiri

<400> SEQUENCE: 5

Tyr Cys Leu Leu Phe Leu Ile Asn Gly Cys
1               5                   10


<210> SEQ ID NO 6
<211> LENGTH: 13
<212> TYPE: PRT
<213> ORGANISM: Herpesvirus saimiri

<400> SEQUENCE: 6

Ser Ser Val Ile Leu Cys Val Phe Ser Asn Met Leu Cys
1               5                   10


<210> SEQ ID NO 7
<211> LENGTH: 10
<212> TYPE: PRT
<213> ORGANISM: Molluscum contagiosum virus
```

```
<400> SEQUENCE: 7

Ser Leu Leu Leu Phe Leu Cys His Asp Ala
1               5                   10


<210> SEQ ID NO 8
<211> LENGTH: 12
<212> TYPE: PRT
<213> ORGANISM: Molluscum contagiosum virus

<400> SEQUENCE: 8

Ser Arg Phe Val Glu Leu Val Leu Ala Leu Glu Asn
1               5                   10
```